US009000187B2

(12) United States Patent
Meng

(10) Patent No.: US 9,000,187 B2
(45) Date of Patent: Apr. 7, 2015

(54) PARASITICIDAL COMPOSITIONS COMPRISING BENZIMIDAZOLE DERIVATIVES, METHODS AND USES THEREOF

(71) Applicant: Charles Q Meng, Johns Creek, GA (US)

(72) Inventor: Charles Q Meng, Johns Creek, GA (US)

(73) Assignee: Merial, Inc., Duluth, GA (US)

( * ) Notice: Subject to any disclaimer, the term of this patent is extended or adjusted under 35 U.S.C. 154(b) by 0 days.

(21) Appl. No.: 13/865,802

(22) Filed: Apr. 18, 2013

(65) Prior Publication Data

US 2013/0281392 A1 Oct. 24, 2013

Related U.S. Application Data

(60) Provisional application No. 61/635,961, filed on Apr. 20, 2012.

(51) Int. Cl.

| | |
|---|---|
| ***C07D 235/10*** | (2006.01) |
| ***C07D 235/28*** | (2006.01) |
| ***C07D 235/08*** | (2006.01) |
| ***C07D 405/10*** | (2006.01) |
| ***C07D 409/10*** | (2006.01) |
| ***A61K 45/06*** | (2006.01) |
| ***A61K 31/4184*** | (2006.01) |
| ***A61K 31/277*** | (2006.01) |
| ***C07D 235/18*** | (2006.01) |

(52) U.S. Cl.

CPC ............ *C07D 235/28* (2013.01); *C07D 235/10* (2013.01); *C07D 235/08* (2013.01); *C07D 405/10* (2013.01); *C07D 409/10* (2013.01); *A61K 45/06* (2013.01); *A61K 31/4184* (2013.01); *A61K 31/277* (2013.01); *C07D 235/18* (2013.01)

(58) Field of Classification Search

USPC ............................................ 548/310.4, 304.4

See application file for complete search history.

(56) References Cited

U.S. PATENT DOCUMENTS

| | | | | |
|---|---|---|---|---|
| 3,075,975 | A * | 1/1963 | Phillips et al. | 546/187 |
| 3,749,789 | A | 7/1973 | Fisher | |
| 3,987,181 | A | 10/1976 | Traber et al. | |
| 4,197,307 | A | 4/1980 | Gallay et al. | |
| 5,278,181 | A * | 1/1994 | Townsend et al. | 514/395 |
| 7,759,381 | B2 * | 7/2010 | Lee et al. | 514/406 |
| 2010/0130737 | A1 * | 5/2010 | Itoh et al. | 544/165 |

FOREIGN PATENT DOCUMENTS

| | | | |
|---|---|---|---|
| DE | 2016622 | A1 | 10/1971 |
| JP | 1 135773 | A | 5/1989 |
| WO | WO-2010/146083 | A1 * | 12/2010 |

OTHER PUBLICATIONS

PubChem CID 198632, created Aug. 9, 2005.*

PubChem CID 23131923, created Dec. 6, 2007.*

PubChem CID 25184655, created Mar. 16, 2009.*

PubChem CID 50994111, created Apr. 4, 2011.*

Perez-Villanueva, Jaime et al: Structure-activity relationships of benzimidazole derivatives as antiparasitic agents: Dual activity-difference (DAD) maps•, MEDCHEMCOMM , 2(1), 44-49 CODEN: MCCEAY; ISSN: 2040-2503, 2011, XP009170027.

Perez-Villanueva, Jaime et al: Towards a systematic characterization of the antiprotozoal activity landscape of benzimidazole derivatives•, Bioorganic & Medicinal Chemistry , 18(21), 7380-7391 CODEN: BMECEP; ISSN: 0968-0896, 2010, XP027415393.

Kazimierczuk, Z. et al: "Synthesis and antimycobacterial activity of 2-substituted halogenobenzimidazoles", European Journal of Medicinal Chemistry , 40(2), 203-208 CODEN: EJMCA5; ISSN: 0223-5234, 2005, XP027857753.

Hernandez-Luis, Francisco et al: "Synthesis and biological activity of 2-(trifluoromethyl)-1H-benzimidazole derivatives against some protozoa and *Trichinella spiralis*", European Journal of Medicinal Chemistry , 45(7), 3135-3141 CODEN: EJMCA5; ISSN: 0223-5234, 2010, XP0027050440.

Navarrete-Vazquez, G. et'al: 'Al: "Synthesis and antiparasitic activity of 2-(trifluoromethyl)benzimidazole derivatives", Bioorganic & Medicinal Chemistry Letters , 11(2), 187-190 CODEN: BMCLE8; ISSN: 0960-894X, 2001, XP004314844.

Hernandez-Luis, Francisco et al: "Synthesis and biological activity of 2-(trifluoromethyl)-1H-benzimidazole derivatives against some protozoa and *Trichinella spiralis*", XP027050440, retrieved from STN Database accession No. 2010:619036.

Rojas-Aguirre, Yareli et al: "Studies on 6-chloro-5-(1-naphthyloxy)-2-(trifluoromet hyl)-1Hbenzimidazole/ 2-hydroxypropyl-.beta.-cyclo dextrin association: Characterization, molecular modeling studies, and in vivo", Bioorganic & Medicinal Chemistry , 19(2), 789-797 CODEN: BMECEP; ISSN: 0968-0896, 2011, XP009170199.

Chomicz, Lidia et al: "Anti-*Pentatrichomonas hominis* activity of newly synthesized benzimidazole derivatives—in vitro studies", ACTA Parasitologica , 54(2), 165-171 CODEN: ACTPEO; ISSN: 1230-2821, 2009, XP009170028.

Diaz-Chiguer, Dylan L. et al: "In vitro and in vivo trypanocidal activity of some benzimidazole derivatives against two strains of *Trypanosoma cruzi*", ACTA Tropica, 122(1), 108-112 CODEN: ACTRAQ; ISSN: 0001-706X, 2012, XP009170026.

* cited by examiner

*Primary Examiner* — Laura L. Stockton

(74) *Attorney, Agent, or Firm* — Judy Jarecki-Black; James Corbitt; Merial, Inc.

(57) ABSTRACT

The invention relates to oral, topical or injectable compositions for combating liver fluke parasites in mammals, comprising at least one benzimidazole derivative active agent. The invention also provides for an improved method for eradicating and controlling liver fluke parasite infections and infestations in a mammal comprising administering the compositions of the invention to the mammal in need thereof.

32 Claims, No Drawings

PARASITICIDAL COMPOSITIONS COMPRISING BENZIMIDAZOLE DERIVATIVES, METHODS AND USES THEREOF

This application claims priority to U.S. Provisional Patent Application No. 61/635,961, filed Apr. 20, 2012.

FIELD OF THE INVENTION

The present invention provides oral, topical or injectable veterinary compositions comprising a benzimidazole derivative active agent for controlling liver flukes in mammals. The use of these compounds and compositions against liver flukes and methods for treating parasitic infections and infestations in mammals is presented herein.

BACKGROUND OF THE INVENTION

Animals such as mammals (including humans) are often susceptible to parasite infections and infestations. These parasites may be ectoparasites, such as insects, and endoparasites such as filariae and other worms. Production animals, such as cows, pigs, sheep and goats, can be infected with one or more trematodes. Of particular concern here is *Fasciola hepatica* (i.e., liver fluke or *F. hepatica*).

Liver flukes are a particular problem because they adversely affect the health of the animal or human and can inflict significant economic loss in a domestic livestock population. It is estimated that *F. hepatica* poses a risk to at least 250 million sheep and 350 million cattle worldwide. Moreover, domestic animals other than sheep and cows may serve as intermediate hosts. Liver flukes can cause liver condemnation, secondary infections, reduced milk and meat production, abortion and fertility problems.

Several types of control measures for liver flukes have been introduced over the past century. First, halogenated hydrocarbons (e.g., $CCl_4$; carbon tetrachloride) were introduced for ruminants in the 1920s. Halogenated hydrocarbons had limited success and are no longer used primarily because of their adverse effects and variable efficacy. Second, halogenated phenols were administered in the late 1950s (e.g., hexachlorophene and bithionol sulfoxide) followed by the similar halogenated salicylanilides (e.g., oxyclozanide, bromoxanide). Fourth, benzimidazole carbamates (e.g., albendazole, luxabendazole) were found to have a broad anthelmintic spectrum against nematodes and mature *F. hepatica*. Another benzimidazole—the chlorinated methylthiobenzimidazole derivative triclabendazole—has a high success rate against *F. hepatica*. Fifth, bisanilino compounds introduced in the 1960s were intolerable due to toxic side effects. Finally, benzene sulfonamides (e.g., clorsulon) were studied in the 1970s. Extensively modified examples of this class demonstrate high efficacy on both mature and immature *F. hepatica*. Of these six classes of anthelmintics the benzimidazole class is perhaps the most widely used for its high efficacy.

The benzimidazole anthelmintics are widely used to treat internal worm parasites. U.S. Pat. No. 4,197,307 discloses 6-phenyl substituted benzimidazoles useful for treating trematodes. The '307 patent discloses a substitution from the sulfur atom at the 2-position of the imidazole ring as well as a substituted aryloxy or thioaryl group from the 6-position of the benzene ring.

U.S. Pat. No. 4,205,077 discloses benzimidazole sulfides as anthelmintic agents. While claiming the same basic 6-phenyl substituted structure of the '307 patent, the '077 patent differs in that the sulfur at the 2-position of the imidazole ring is not substituted, leaving it available to form a dimer linked by a disulfide bond.

U.S. Pat. No. 4,336,262 discloses a pour-on anthelmintic that is heavily substituted at the 7-position of the benzimidazole ring. In particular, the substitution is a sulfamoyl moiety while the 5- and 6-positions are minimally substituted.

U.S. Pat. No. 4,468,390 discloses an anthelmintic composition that is a mixture of a macrolide antibiotic and one of a benzimidazole, a salicylamide or an isoquinoline compound. The benzimidazole compounds disclosed as suitable for use in the '390 patent are 2-(methoxycarbonylamino)benzimidazole, 5-butyl-2-(methoxycarbonylamino)benzimidazole, 5-propoxy-2-(methoxycarbonylamino)benzimidazole, 5-ethoxy-2-ethoxycarbonyl-aminobenzimidazole, 5-propylthio-2-(methoxycarbonylamino)benzimidazole, 5-phenylthio-2-(methoxycarbonylamino)benzimidazole, 5-phenylsulphinyl-2-(methoxycarbonylamino)benzimidazole, 5-(2,4-dichlorophenoxy)-6-chloro-2-methylthiobenzimidazole, 6-chloro-5-(2,3-dichlorophenoxy)-2-methylthiobenzimidazole, 2-(4-thiazolyl)benzimidazole, and 5-isopropoxycarbonylamino-2-(4-thiazolyl)benzimidazole, however, data is provided only for albendazole (i.e., 5-propylthio-2-methoxycarbonyl-aminobenzimidazole).

Indeed, triclabendazole is the current drug of choice against mature and immature liver flukes. Not surprisingly, however, reports of parasite resistance are increasing. For example, Mottier et al., report that a population of resistant *F. hepatica* (Sligo) may use an altered influx/efflux mechanism to selectively decrease the amount of triclabendazole and triclabendazole sulfoxide but not albendazole. See Mottier et al., *J. Parasitol.*, 92(6), 2006, pp. 1355-1360. McConville et al., report that juvenile triclabendazole-resistant *F. hepatica* are somewhat susceptible to compound alpha (i.e., 5-chloro-2-methylthio-6-(1-naphthyloxy)-1H-benzimidazole) via a tubulin-independent mechanism. See McConville et al., Parasitol. Res., (2007) 100:365-377. Further, Keiser et al., report the testing of artemether and OZ78 in triclabendazole-resistant *F. hepatica*, although at high concentrations. For a short review of triclabendazole resistance see Brennan et al., Experimental and Molecular Pathology, 82, (2007) pp. 104-109.

The resistance to triclabendazole and lack of effective substitutes creates a pressing need in the field for alternatives that exhibit low side effects and that do not contaminate the animals as a food source. Optimal compositions should further be efficacious, have a quick onset of activity, have a long duration of activity, and be safe to the animal recipients and their human owners.

INCORPORATION BY REFERENCE

Any abovementioned applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

The present invention is directed to compounds for treating helminth infestation comprising an anthelmintically effective amount of benzimidazole compounds of formula (I), formula (II), or formula (III) described herein and their use to control parasites in mammals to include humans. In accordance with this invention, it has been discovered that these compounds show unexpected efficacy and speed of onset.

The invention encompasses uses or veterinary uses of the oral, topical or injectable benzimidazole compositions comprising an anthelmintically effective amount of benzimidazole compounds of formula (I), formula (II), or formula (III), for the treatment or prophylaxis of parasitic trematode infections and infestations of animals (either wild or domesticated), including livestock and companion animals such as cats, dogs, horses, sheep, goats, pigs and cattle, with the aim of ridding these hosts of liver flukes encountered by such animals. The composition may also be suitable for humans.

The invention also provides methods for treating helminth infestation comprising administration of an anthelmintically effective amount of the compound(s) of formula (I), formula (II), or formula (III), to an animal in need thereof. Surprisingly, it has been found that the inventive compositions and formulations described herein exhibit superior efficacy against *F. hepatica* compared to compositions known in the art.

The invention does not intentionally seek to encompass any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product. The invention and its embodiments are disclosed by the following Detailed Description.

DETAILED DESCRIPTION

In this disclosure and in the claims, terms such as "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

It is also noted that in this disclosure and in the claims and/or paragraphs, the compounds of the invention are intended to include all stereoisomers and crystalline forms (which includes hydrated forms, polymorphic forms and amorphous forms with up to 15% by weight crystalline structure) thereof.

Definitions

Terms used herein will have their customary meaning in the art unless specified otherwise. The organic moieties mentioned in the definitions of the variables of formula (I) are—like the term halogen—collective terms for individual listings of the individual group members. The prefix $C_n$—$C_m$ indicates in each case the possible number of carbon atoms in the group.

The term "animal" is used herein to include all mammals and also include all vertebrate animals. Animals include, but are not limited to, cats, dogs, cattle, cows, deer, goats, horses, llamas, pigs, sheep and yaks. It also includes an individual animal in all stages of development, including embryonic and fetal stages. In some embodiments, the animal may be a human animal.

The term "alkyl" refers to saturated straight, branched, cyclic, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups or "cycloalkyl", which are encompassed by alkyl include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

Terms including the term "alkyl" such as "alkylcycloalkyl," "cycloalkylalkyl," "alkylamino," or "dialkylamino" will be understood to comprise an alkyl group as defined above linked to the other functional group, where the group is linked to the compound through the last group listed, as understood by those of skill in the art.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "alkylthio" refers to alkyl-S—, wherein alkyl is as defined above. Similarly, the terms "haloalkylthio," "cycloalkylthio," and the like, refer to haloalkyl-S— and cycloalkyl-S— where haloalkyl and cycloalkyl are as defined above.

The term "alkylsulfinyl" refers to alkyl-S(O)—, wherein alkyl is as defined above. Similarly, the term "haloalkylsulfinyl" refers to haloalkyl-S(O)— where haloalkyl is as defined above.

The term "alkylsulfonyl" refers to alkyl-$S(O)_2$—, wherein alkyl is as defined above. Similarly, the term "haloalkylsulfonyl" refers to haloalkyl-$S(O)_2$— where haloalkyl is as defined above.

The term alkylamino and dialkylamino refer to alkyl-NH— and $(alkyl)_2N$— where alkyl is as defined above. Similarly, the terms "haloalkylamino" refers to haloalkyl-NH— where haloalkyl is as defined above.

The terms "alkylcarbonyl," "alkoxycarbonyl," "alkylaminocarbonyl," and "dialkylaminocarbonyl refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxycarbonyl," "haloalkylaminocarbonyl," and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl) amino, di(alkenyl)-amino, di(alkynyl)amino, or trialkylsilyl.

The term "aralkyl" refers to an aryl group that is bonded to the parent compound through a diradical alkylene bridge, $(—CH_2—)_n$, where n is 1-12 and where "aryl" is as defined above.

"Heteroaryl" refers to a monovalent aromatic group of from 1 to 15 carbon atoms, such as from 1 to 10 carbon atoms, having one or more oxygen, nitrogen, and sulfur heteroatoms within the ring, for example 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Heteroaryls may include pyridyl, piridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, such as 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Halogen means the atoms fluorine, chlorine, bromine and iodine. The designation of "halo" (e.g., as illustrated in the term haloalkyl) refers to all degrees of substitutions from a single substitution to a perhalo substitution (e.g., as illustrated with methyl as chloromethyl ($—CH_2Cl$), dichloromethyl ($—CHCl_2$), trichloromethyl ($—CCl_3$)).

Stereoisomers and Polymorphic Forms

It will be appreciated by those of skill in the art that certain compounds within the compositions of the invention may exist and be isolated as optically active and racemic forms. Compounds having one or more chiral centers, including at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds within the compositions of the invention may include one or more chiral centers, which results in a theoretical number of optically active isomers. Where compounds within the compositions of the invention include "n" chiral centers, the compounds may comprise up to $2^n$ opticalisomers. The present invention encompasses the specific enantiomers or diastereomers of each compound as well as mixtures of different enantiomers and/or diastereomers of the compounds of the invention that possess the useful properties described herein. The optically active forms can be prepared by, for example, resolution of the racemic forms by selective crystallization techniques, by synthesis from optically active precursors, by chiral synthesis, by chromatographic separation using a chiral stationary phase or by enzymatic resolution.

The compounds within the compositions of present invention may also be present in different solid forms such as different crystalline forms or in the form of an amorphous solid. The present invention encompasses different crystalline forms as well as amorphous forms of the inventive compounds.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents.

Salts

Also contemplated within the scope of the invention are acid or base salts, where applicable, of the compounds of the invention provided for herein.

The term "acid" contemplates all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH_4^+$), alkyl- and dialkylammonium salts, and salts of cyclic amines such as the morpholine and piperidine salts.

The term "derivative" contemplates a compound obtained from or closely related to another substance or compound. A derivative contemplates a chemical compound that may be produced from another chemical compound of similar structure in one or more steps.

In one embodiment, the invention provides novel oral, topical or injectable veterinary compounds according to formula (I) below.

(I)

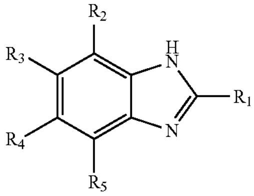

wherein:

$R_1$ is ($C_1$-$C_6$)-alkyl, ($C_2$-$C_5$)-alkenyl, or ($C_2$-$C_5$)-alkynyl, each independently unsubstituted or substituted with two or more halogens; $R_2$ is H or halogen; $R_3$ is halogen, ($C_1$-$C_6$)-alkyl, ($C_2$-$C_5$)-alkenyl, or ($C_2$-$C_5$)-alkynyl, ($C_1$-$C_6$)-alkoxy, thienyl, furanyl, biphenyl, naphthyl, aryl, aryl ether, sulfonylaryl, sulfoxyaryl, thioaryl, $C_3$-$C_6$ cycloalkyl, or tetralin ether; wherein the last seven substituents may be unsubstituted or substituted with one or more of halogen, ($C_1$-$C_3$)-haloalkyl, ($C_1$-$C_3$)-haloalkoxy or carboxyl; $R_4$ is H or halogen and $R_5$ is H or halogen.

In another embodiment, the compound of formula (I) defines $R_1$ as ($C_1$-$C_4$)-alkyl substituted with fluorine. In yet another embodiment, the compound of formula (I) defines $R_2$ as chlorine.

In another embodiment, the compound of formula (I) defines $R_3$ as a mono- or bi-halo substituted phenyl ether. In another embodiment, the compound of formula (I) defines $R_3$ as a bi-or tri-halo substituted phenyl. In yet another embodiment, the compound of formula (I) defines $R_3$ as chlorine, bromine or fluorine.

In another embodiment, the compound of formula (I) defines $R_4$ as chlorine. In another embodiment, the compound of formula (I) defines $R_5$ as hydrogen.

In another embodiment, the compound of formula (I) is 6-chloro-5-(4-chlorophenyl)-2-trifluoromethylbenzimidazole. In another embodiment, the compound of formula (I) is 6-chloro-5-(2,3-dichlorophenoxy)-2-heptafluoropropylbenzimidazole. In another embodiment, the compound of formula (I) is 6-chloro-5-(3,5-dichlorophenyl)-2-trifluoromethylbenzimidazole. In another embodiment, the compound of formula (I) is 6-chloro-5-(3,4-dichlorophenyl)-2-trifluoromethylbenzimidazole. In another embodiment, the compound of formula (I) is 6-chloro-5-(2,4-dichlorophenyl)-2-trifluoromethylbenzimidazole. In another embodiment, the compound of formula (I) is 6-chloro-5-(2,3,5-trichlorophenyl)-2-trifluoromethylbenzimidazole.

In another aspect, the invention is a composition for treating helminth infestation comprising an anthelmintically effective amount of the compounds of formula (I) defined above and a pharmaceutically acceptable carrier.

In another embodiment, the composition including formula (I) is combined with a macrocyclic lactone. In one embodiment, the macrocyclic lactone is an avermectin. In another embodiment, the macrocyclic lactone is ivermectin.

In yet another embodiment, the composition including formula (I) is combined with verapamil. Verapamil and macrocyclic lactones such as avermectins may provide a synergistic effect in combination with compounds of formula (I) to kill triclabendazole-resistant liver flukes. The synergistic effect is thought to occur due to the inhibition of the P-glycoprotein drug transporter by verapamil or the avermectin.

In another aspect, the invention is a method for treating helminth infestation comprising administration of an anthelmintically effective amount of the compounds defined above to an animal in need thereof. The helminths are, for example, trematodes, and may be specifically *F. hepatica.*

In yet another embodiment, the invention provides novel oral, topical or injectable veterinary compounds according to formula (II) below.

(II)

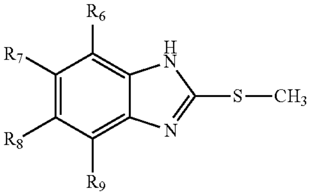

wherein:

$R_6$ is H;

$R_7$ is ($C_1$-$C_6$)-alkyl, ($C_2$-$C_5$)-alkenyl, or ($C_2$-$C_5$)-alkynyl, ($C_1$-$C_6$)-alkoxy, tetralin ether, bromophenoxy, phenoxy, sulfonylaryl, sulfoxyaryl, thioaryl, or ($C_3$-$C_6$)-cycloalkyl;

wherein the last four substituents may be unsubstituted or substituted with one or more of halogen or ($C_1$-$C_3$)-alkyl; and wherein phenoxy is substituted with one or more of ($C_1$-$C_3$)-alkyl or trifluoromethoxy; $R_8$ is H or halogen; and $R_9$ is H.

In one embodiment, the compound of formula (II) defines $R_7$ as phenoxy substituted with one or more methyl groups. In another embodiment, the compound of formula (II) defines $R_7$ as 2-bromophenoxy. In another embodiment, the compound of formula (II) defines $R_8$ as chlorine or fluorine.

In one embodiment, the compound of formula (II) is 6-chloro-5-(2,3-dimethylphenoxy)-2-methylthiobenzimidazole. In another embodiment, the compound of formula (II) is 6-chloro-5-(2-bromophenoxy)-2-methylthiobenzimidazole. In another embodiment, the compound of formula (II) is 6-chloro-5-hexyl-2-methylthiobenzimidazole.

In another aspect, the invention is a composition for treating helminth infestation comprising an anthelmintically effective amount of the compounds of formula (II) defined above and a pharmaceutically acceptable carrier.

In another embodiment, the composition including formula (II) is combined with a macrocyclic lactone. In one embodiment, the macrocyclic lactone is an avermectin. In another embodiment, the macrocyclic lactone is ivermectin.

In yet another embodiment, the composition including formula (II) is combined with verapamil. Verapamil and macrocyclic lactones such as avermectins may provide a synergistic effect in combination with compounds of formula (II) to kill triclabendazole-resistant liver flukes. The synergistic effect is thought to occur due to the inhibition of the P-glycoprotein drug transporter by verapamil or the avermectin.

In yet another aspect, the invention is a method for treating helminth infestation comprising administration of an anthelmintically effective amount of the compounds of formula (II) to an animal in need thereof. The helminths are, for example, trematodes and may be specifically *F. hepatica*.

In yet another embodiment, the invention provides novel oral, topical or injectable veterinary compounds according to formula (III) below.

(III)

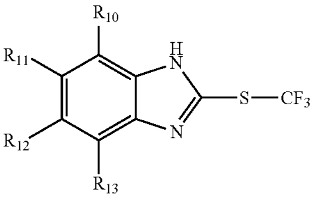

wherein:

$R_{10}$ is H;

$R_{11}$ is ($C_1$-$C_6$)-alkyl, ($C_2$-$C_5$)-alkenyl, ($C_2$-$C_5$)-alkynyl, ($C_1$-$C_6$)-alkoxy, tetralin ether, aryl, aryl ether, sulfonylaryl, sulfoxyaryl, thioaryl, or ($C_3$-$C_6$)-cycloalkyl;

wherein the last six substituents may be unsubstituted or substituted with one or more of ($C_1$-$C_6$)-alkyl, halogen, ($C_1$-$C_3$)-haloalkyl, or ($C_1$-$C_3$)-haloalkoxy;

$R_{12}$ is H or halogen; and $R_{13}$ is H.

In one embodiment, the compound of formula (III) defines aryl as naphthyl, biphenyl or phenyl. In another embodiment, the compound of formula (III) defines $R_{11}$ as phenoxy substituted with one or more halogens.

In one embodiment, the compound of formula (III) is 6-chloro-5-(2,3-dichlorophenoxy)-2-trifluoromethylthiobenzimidazole. In another embodiment, the compound of formula (III) is 6-chloro-5-(4-chlorophenyl)-2-trifluoromethylthiobenzimidazole. In another embodiment, the compound of formula (III) is 6-chloro-5-(3-chlorophenyl)-2-trifluoromethylthiobenzimidazole. In yet another embodiment, the compound of formula (III) is 6-chloro-5-(2-butyl)-cyclopropyl-2-trifluoromethylthiobenzimidazole.

In another aspect, the invention provides a composition for treating helminth infestation comprising an anthelmintically effective amount of the compound of formula (III) defined above and a pharmaceutically acceptable carrier.

In another embodiment, the composition including formula (III) is combined with a macrocyclic lactone. In one embodiment, the macrocyclic lactone is an avermectin. In another embodiment, the macrocyclic lactone is ivermectin.

In yet another embodiment, the composition including formula (III) is combined with verapamil. Verapamil and macrocyclic lactones such as avermectins may provide a synergistic effect in combination with compounds of formula (III) to kill triclabendazole-resistant liver flukes. The synergistic effect is thought to occur due to the inhibition of the P-glycoprotein drug transporter by verapamil or the avermectin.

In yet another aspect, the invention provides a method for treating helminth infestation comprising administration of an anthelmintically effective amount of the compound of formula (III) defined above to an animal in need thereof. The helminths may be, for example, trematodes and may be specifically *F. hepatica*.

Experimental Procedure and Results

Representative compounds of formula (I), formula (II), and formula (III) were tested in vitro against *F. hepatica* as follows. Adult *F. hepatica* (fluke) were collected from infected bovine livers obtained from a local abattoir (Basel, Switzerland). The worms were quickly washed with 0.9% (w/v) NaCl and placed in 6 or 12-well plates (Costar). Culture medium in each well contained RPMI 1640 (Gibco) at 37° C., which was supplemented with antibiotics (50 μg/ml streptomycin and 50 IU/ml penicillin; Gibco) and 80 μg/ml of a haemin solution. The haemin solution was prepared as follows: 5 mg haemin was dissolved in 1 ml of 0.1M aqueous solution of NaOH, and 3.95 ml of PBS (pH=7.4) and 0.05 ml of 1M HCl were added to adjust the pH to 7.1-7.4 (Keiser and Morson, 2008). Cultures were kept at 37° C. in an atmosphere of 5% $CO_2$. To monitor the temporal effects of test compounds in vitro, 3 flukes were incubated for 72 h in the presence of 50 or 100 μg/ml of each test compound. At 24, 48, and 72 h, worms were examined using a dissecting microscope. For the adult worms, a viability scale ranging from 4 (normal movements) to 1 (death; no movement observed for two min using a microscope) was used. Test compounds that showed activity at a concentration of 50 μg/ml were further evaluated at lower concentrations (20 μg/ml, 10 μg/ml, 5 μg/ml and 2.5 μg/ml).

Table 1 lists representative compounds of formula (I) of the present invention and their effective in vitro concentrations against *F. hepatica*. All compounds were tested in vitro on the adult stage of *F. hepatica* as described above. Each data point refers to at least two independent experiments. For Table 1, $R_2$ is H, $R_4$ is Cl and $R_5$ is H.

(I)

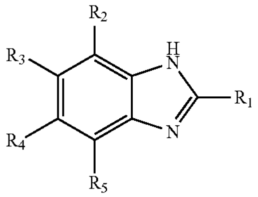

TABLE 1

| Compound No. | $R_1$ | $R_3$ | Effective in vitro concentration; μg/mL |
|---|---|---|---|
| 114 | $CF_3$ | 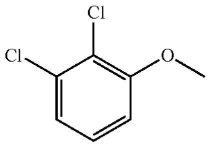 | 5 |
| 115 | $CHF_2$ | 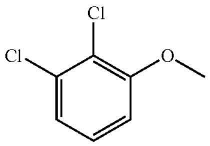 | TBD |
| 116 | $C_2F_5$ | 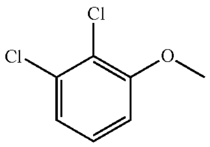 | TBD |

TABLE 1-continued
| Compound No. | $R_1$ | $R_3$ | Effective in vitro concentration; μg/mL |
|---|---|---|---|
| 130 | $CF_3$ | 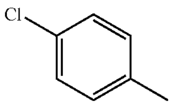 | 2.5 |
| 132 | $CH_3$ | 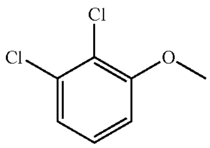 | 50 |
| 133 | $CH_2CH_3$ | 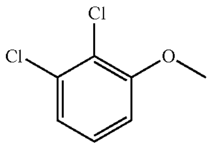 | 50 |
| 134 | $(CH_2)_2CH_3$ | 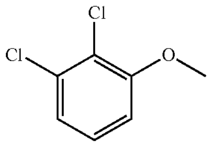 | 50 |
| 135 | $(CH_2)_3CH_3$ | 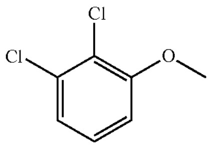 | 50 |
| 136 | $CH(CH_3)_2$ | 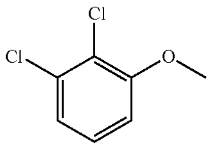 | 50 |
| 137 | $CH(CH_3)CH_2CH_3$ | 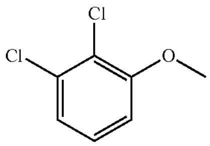 | 20 |
| 138 | $CH_2CH(CH_3)_2$ | 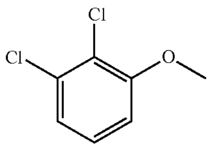 | 50 |
| 139 | $C(CH_3)_3$ | 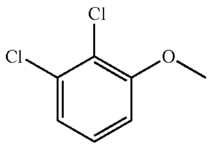 | 50 |
TABLE 1-continued
| Compound No. | $R_1$ | $R_3$ | Effective in vitro concentration; μg/mL |
|---|---|---|---|
| 140 | $C_3F_7$ | 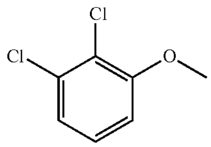 | 5 |
| 141 | $C_4F_9$ | 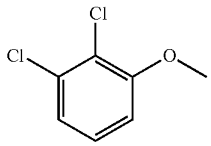 | 10 |
| 150 | $CF_3$ | 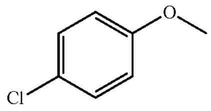 | 50 |
| 151 | $CF_3$ | 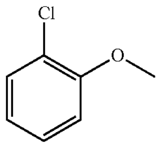 | 50 |
| 174 | $CF_3$ | 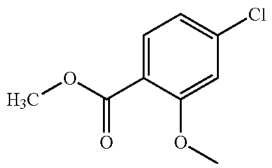 | 50 |
| 195 | $CF_3$ | 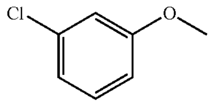 | 20 |
| 196 | $CF_3$ | 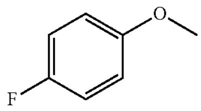 | 10 |
| 199 | $CF_3$ | 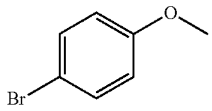 | 20 |
| 203 | $CF_3$ | 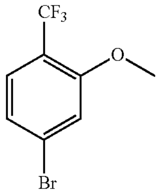 | <100 |
| 220 | $CF_3$ | 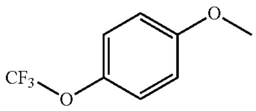 | 20 |

TABLE 1-continued
| Compound No. | $R_1$ | $R_3$ | Effective in vitro concentration; μg/mL |
|---|---|---|---|
| 236 | $CF_3$ | 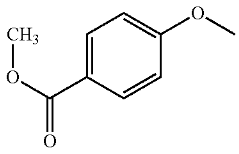 | 20 |
| 237 | $CF_3$ | 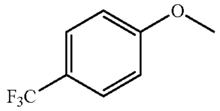 | 10 |
| 245 | $CF_3$ | 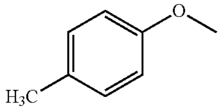 | 50 |
| 247 | $CF_3$ | 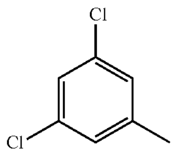 | 5 |
| 248 | $CF_3$ | 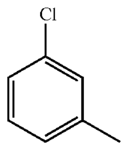 | 10 |
| 249 | $CF_3$ | 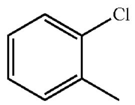 | 10 |
| 254 | $CF_3$ | 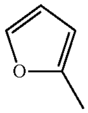 | 20 |
| 255 | $CF_3$ | 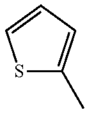 | 50 |
| 256 | $CF_3$ | 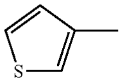 | 50 |
| 258 | $CF_3$ | 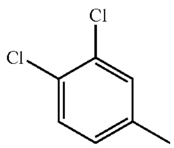 | 5 |
| 259 | $CF_3$ | 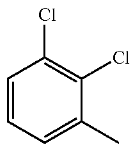 | 20 |
TABLE 1-continued
| Compound No. | $R_1$ | $R_3$ | Effective in vitro concentration; μg/mL |
|---|---|---|---|
| 260 | $CF_3$ | 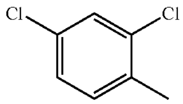 | 5 |
| 261 | $CF_3$ | 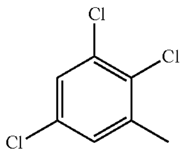 | 5 |
| 262-100 | $C_2F_5$ | 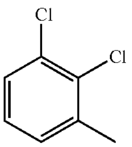 | 10 |
| 273 | $C_3F_7$ | 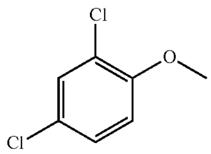 | 5 |
| 274 | $C_3F_7$ | 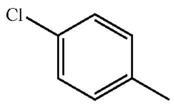 | 5 |
| 275 | $CF_3$ | 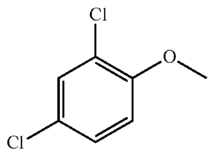 | 10 |
| 276 | $C_2F_5$ | 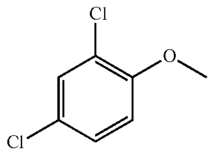 | <5 |
| 277 | $CF_3$ | 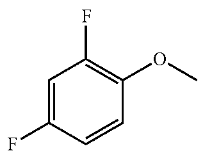 | 10 |
| 278 | $C_2F_5$ | 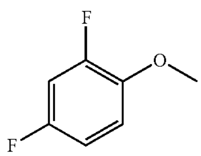 | <5 |

TABLE 1-continued
| Compound No. | $R_1$ | $R_3$ | Effective in vitro concentration; μg/mL |
|---|---|---|---|
| 279 | $C_3F_7$ | 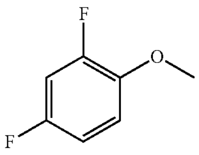 | <5 |
| 280 | $CF_3$ | 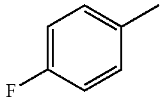 | 20 |
| 281 | $C_2F_5$ | 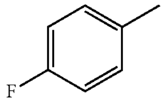 | 5 |
| 282 | $C_3F_7$ | 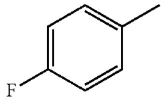 | <2.5 |
| 283 | $C_2F_5$ | 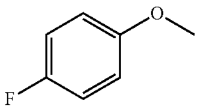 | <2.5 |
| 284 | $C_3F_7$ | 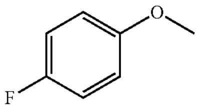 | 5 |
| 285 | $C_2F_5$ | 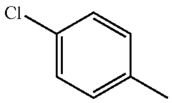 | 20 |
| 286 | $CF_3$ | 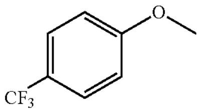 | 20 |
| 287 | $C_2F_5$ | 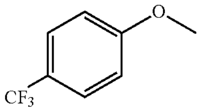 | 50 |
| 288 | $C_3F_7$ | 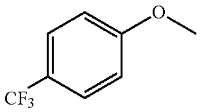 | 20 |
| 289 | $C_2F_5$ | 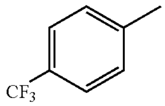 | <2.5 |
| 290 | $C_3F_7$ | 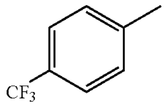 | 50 |
TABLE 1-continued
| Compound No. | $R_1$ | $R_3$ | Effective in vitro concentration; μg/mL |
|---|---|---|---|
| 291 | $C_3F_7$ | 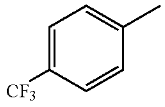 | 20 |
| 295 | $CF_3$ | 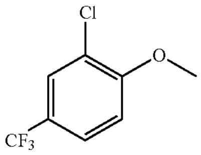 | <10 |
| 296 | $C_2F_5$ | 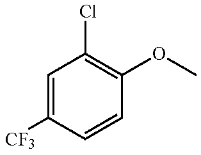 | <2.5 |
| 297 | $C_3F_7$ | 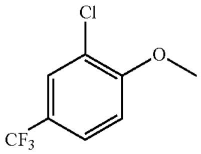 | 50 |
| 301 | $CF_3$ | 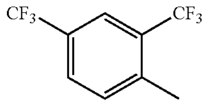 | <10 |
| 302 | $C_2F_5$ | 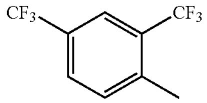 | <2.5 |
| 303 | $C_3F_7$ | 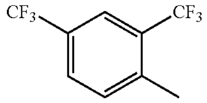 | 20 |
| 304 | $CF_3$ | 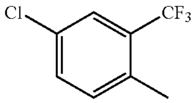 | 20 |
| 305 | $C_2F_5$ | 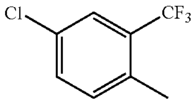 | 20 |
| 306 | $C_3F_7$ | 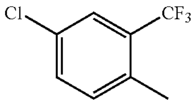 | 20 |
| 307 | $CF_3$ | 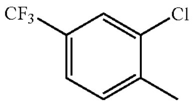 | <2.5 |

TABLE 1-continued

| Compound No. | $R_1$ | $R_3$ | Effective in vitro concentration; µg/mL |
|---|---|---|---|
| 308 | $C_2F_5$ | 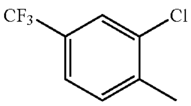 | <10 |
| 309 | $C_3F_7$ | 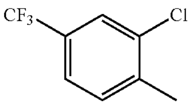 | 20 |

Table 2 lists representative compounds of formula (II) of the present invention and their effective in vitro concentrations against *F. hepatica*. All compounds were tested in vitro on the adult stage of *F. hepatica* as described above. Each data point refers to at least two independent experiments. For Table 2 compounds, the 2-position of the benzimidazole ring is methylthio, $R_6$ is H and $R_9$ is H.

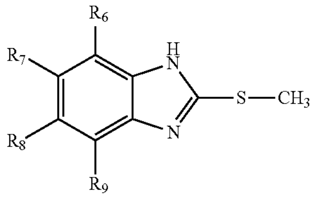

(II)

| Compound No. | $R_7$ | $R_8$ | Effective in vitro concentration; µg/mL |
|---|---|---|---|
| 007 | 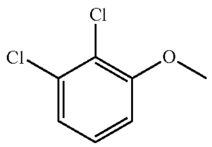 | F | 100 |
| 011 | 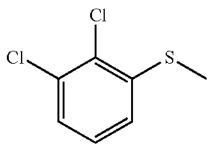 | Cl | 100 |
| 012 | 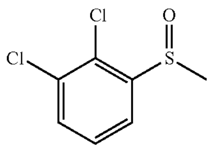 | Cl | 100 |
| 014 | 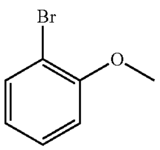 | Cl | 50 |

-continued

| Compound No. | $R_7$ | $R_8$ | Effective in vitro concentration; µg/mL |
|---|---|---|---|
| 015 | 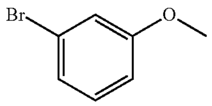 | Cl | 50 |
| 016 | 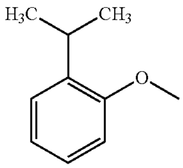 | Cl | TBD |
| 018 | 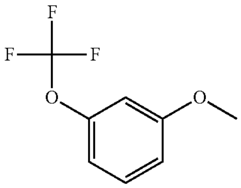 | Cl | 100 |
| 019 | 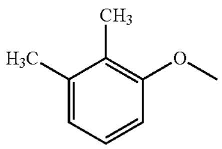 | Cl | 20 |
| 024 | 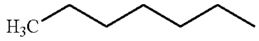 | Cl | 50 |
| 024-4 | 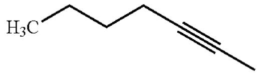 | Cl | 50 |
| 025 | 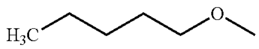 | Cl | 100 |
| 026 | 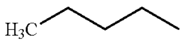 | H | 100 |
| 028 | 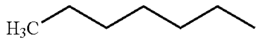 | H | 50 |
| 029 | 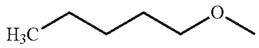 | H | 100 |
| 048 | 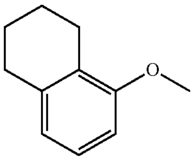 | Cl | 100 |
| 050 | 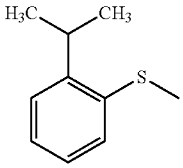 | Cl | 100 |
| 051 | 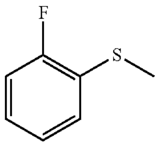 | Cl | 100 |

-continued

| Compound No. | $R_7$ | $R_8$ | Effective in vitro concentration; µg/mL |
|---|---|---|---|
| 063 | 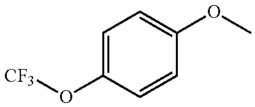 | Cl | TBD |
| 064 | 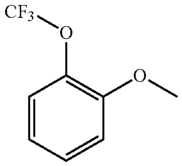 | Cl | TBD |

Table 3 lists representative compounds of formula (III) of the present invention and their effective in vitro concentrations against *F. hepatica*. All compounds were tested in vitro on the adult stage of *F. hepatica* as described above. Each data point refers to at least two independent experiments. For Table 3, the 2-position of the benzimidazole ring is trifluoromethylthio, $R_{10}$ is H and $R_{13}$ is H.

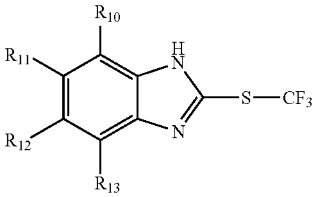

(III)

TABLE 3

| Compound No. | $R_{11}$ | $R_{12}$ | Effective in vitro concentration; µg/mL |
|---|---|---|---|
| 049 | 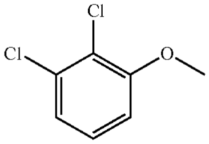 | Cl | 10 |
| 053 | 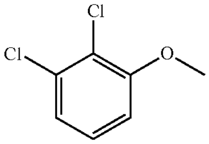 | F | TBD |
| 054 | 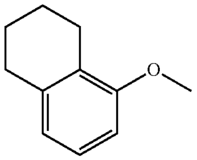 | Cl | TBD |
| 055 | 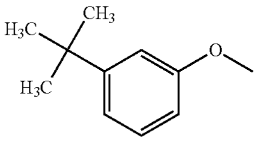 | Cl | TBD |

TABLE 3-continued

| Compound No. | $R_{11}$ | $R_{12}$ | Effective in vitro concentration; µg/mL |
|---|---|---|---|
| 056 | 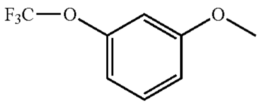 | Cl | TBD |
| 057 | 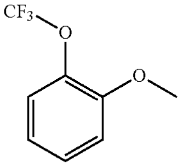 | Cl | TBD |
| 058 | 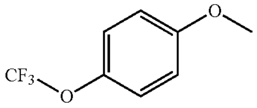 | Cl | TBD |
| 059 | 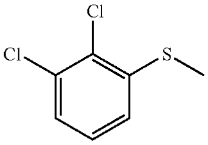 | F | TBD |
| 060 | 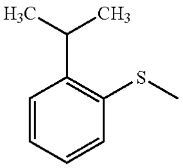 | Cl | TBD |
| 061 | 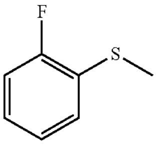 | Cl | TBD |
| 062 | 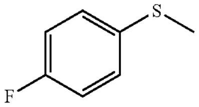 | Cl | TBD |
| 075 | 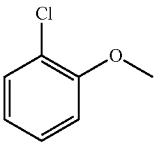 | Cl | TBD |
| 076 | 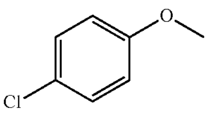 | Cl | TBD |
| 077 | 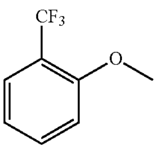 | Cl | TBD |

TABLE 3-continued
| Compound No. | $R_{11}$ | $R_{12}$ | Effective in vitro concentration; μg/mL |
|---|---|---|---|
| 078 | 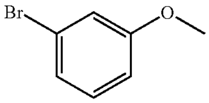 | Cl | TBD |
| 079 | 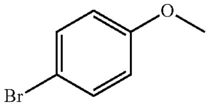 | Cl | TBD |
| 080 | 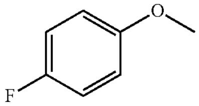 | Cl | TBD |
| 081 | 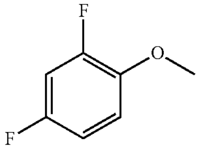 | Cl | TBD |
| 082 | 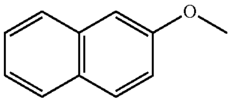 | Cl | TBD |
| 083 | 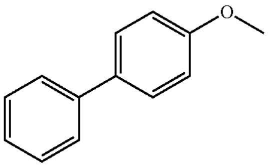 | Cl | TBD |
| 084 | 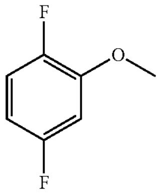 | Cl | TBD |
| 085 | 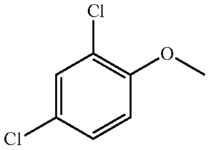 | Cl | TBD |
| 086 | 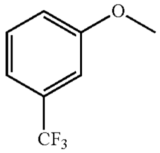 | Cl | TBD |
| 087 | 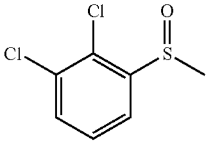 | Cl | 20 |
TABLE 3-continued
| Compound No. | $R_{11}$ | $R_{12}$ | Effective in vitro concentration; μg/mL |
|---|---|---|---|
| 088 | 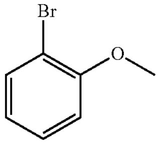 | Cl | TBD |
| 089 | 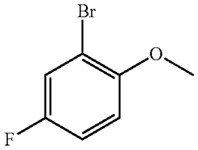 | Cl | TBD |
| 090 | 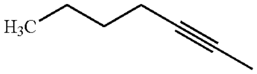 | Cl | TBD |
| 091 | 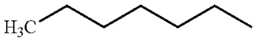 | Cl | TBD |
| 093 | 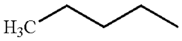 | H | TBD |
| 094 | 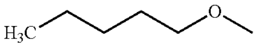 | Cl | TBD |
| 095 | 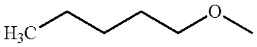 | H | TBD |
| 096 | 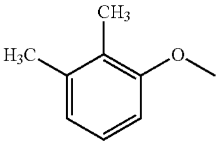 | Cl | TBD |
| 099 | 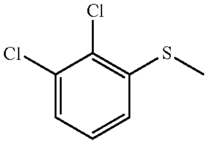 | Cl | TBD |
| 101 | 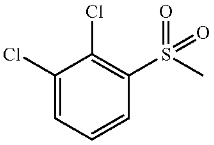 | Cl | 50 |
| 102 | 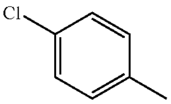 | Cl | 5 |
| 103 | 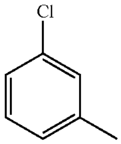 | Cl | 5 |
| 104 | 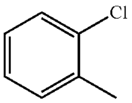 | Cl | 50 |

TABLE 3-continued

| Compound No. | $R_{11}$ | $R_{12}$ | Effective in vitro concentration; μg/mL |
|---|---|---|---|
| 106 | 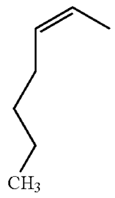 | Cl | 50 |
| 108 | 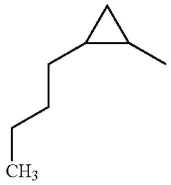 | Cl | 10 |

Select compounds were further tested against a population of *F. hepatica* resistant to triclabendazole (Oberon isolate of Australia). The compounds were tested in vitro as described above but a different scale was used to measure the effect of the flukicide compound. A "3" indicates very active; the whole body moves as observed under a microscope. A "2" indicates less movement and activity is observed under the microscope. A "1" indicates that only some head or tail movement is observed. A "0" indicates death. Compound #273 (see Table 1 for structure) is particularly efficacious even at 10 μg/ml compared with compounds #114, #130, #140 and a 50 μg/ml positive control of triclabendazole/sulfoxide solution.

TABLE 4

| Time | TBZ-SOX (50 μg/ml) | #114 (20 μg/ml) | #130 (20 μg/ml) | #140 (20 μg/ml) | #273 (20 μg/ml) | #273 (10 μg/ml) | Control |
|---|---|---|---|---|---|---|---|
| 0 h | 3 | 3 | 3 | 3 | 3 | 3 | 3 |
| 24 h | 3 | 0.5 | 0.25 | 0.5 | 0 | 0 | 3 |
| 48 h | 2.5 | 0 | 0 | 0 | 0 | 0 | 3 |
| 72 h | 2 | 0 | 0 | 0 | 0 | 0 | 3 |

Additionally, five compounds were tested in vivo in female Wistar rats against an untreated control. Rats were kept in groups of five in type-4 Makrolon cages under environmentally controlled conditions (temperature, 22° C.; humidity, 70%; light/dark cycle, 12/12 h) with free access to water and rodent food. *F. hepatica* metacercariae (Pacific Northwest wild strain) were purchased from Baldwin Aquatics (Monmouth, Oreg.). After one week of adaptation, each rat was infected by oral gavage with approximately 25 metacercariae.

Three rats harboring adult *F. hepatica* (>8 weeks postinfection) were used to test each of five compounds. The rats were given a single oral dose of 100 mg/kg with each of test compounds 273, 274, 282, 290 and 303. Untreated rats (n=3) served as controls. Dosing formulations consisted of 300 ul Tween 80:ethanol (1:1) and 2.7 ml water. One week after dosing the animals were euthanized and live worms recovered from excised bile ducts.

Compounds 303 and 273 showed the greatest reduction in worm burden with 79.4 and 76.2 percent, respectively. Compounds 282 and 274 both lowered the worm burden by more than 60 percent. See Table 5.

TABLE 5

| Treatment | Dose: | No. of rats cured/No. of rats investigated | Number of living worms Ø = average | Worm burden reduction % |
|---|---|---|---|---|
| control Batch 144 | — | 0/3 | 6.3 | 0 |
| 273 | 100 mg/kg | 1/2 | 1.5 | 76.2 |
| 274 | 100 mg/kg | 1/3 | 2.3 | 63.5 |
| 282 | 100 mg/kg | 2/3 | 2 | 68.3 |
| 290 | 100 mg/kg | 1/3 | 3.3 | 47.6 |
| 303 | 100 mg/kg | 1/3 | 1.3 | 79.4 |

Additional veterinary/pharmaceutical active ingredients may be used with the compositions of the invention for oral, topical or injectable use. In some embodiments, the additional active agents may include, but are not limited to, acaricides, anthelmintics, anti-parasitics and insecticides. Anti-parasitic agents can include both ectoparasiticidal and endoparasiticidal agents.

Veterinary pharmaceutical agents that may be included in the compositions of the invention are well-known in the art (see e.g., *Plumb' Veterinary Drug Handbook,* 5$^{th}$ Edition, ed. Donald C. Plumb, Blackwell Publishing, (2005) or *The Merck Veterinary Manual,* 9$^{th}$ Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdenate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, chlorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/−clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium, calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerine (oral), glycopyrrolate, gonadorelin, grisseofulvin, guaifenesin, halothane, hemoglobin glutamer-200 (Oxyglobin®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inaminone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenyloin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/l-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocamide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In another embodiment of the invention, one or more macrocyclic lactones or lactams, which act as an acaricide, anthelmintic agent and/or insecticide, can be added to the compositions of the invention.

The macrocyclic lactones include, but are not limited to, avermectins, such as abamectin, dimadectin, doramectin, emamectin, eprinomectin, ivermectin, latidectin, lepimectin, selamectin, ML-1,694,554 and milbemycins, such as milbemectin, milbemycin D, moxidectin and nemadectin. Also included are the 5-oxo and 5-oxime derivatives of said avermectins and milbemycins. Examples of combinations of benzimidazole compounds with macrocyclic lactones include but may not be limited to those described in U.S. Pat. No. 7,396,820 (Virbac Corp. and Hartz Mountain Corporation), incorporated herein by reference. The '820 patent discloses a combination of fenbendazole with ivermectin along with at least two other active ingredients for the treatment of helminthiasis of mammals, and particularly tapeworm, hookworm, roundworm, whipworm and heartworm. The '820 patent does not contemplate the treatment of trematodes.

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" $12^{th}$ ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In another embodiment, the invention comprises a composition comprising a benzimidazole compound in combination with verapamil. Verapamil is believed to be an inhibitor of P-glycoprotein, which is a membrane protein that has been shown to efflux triclabendazole from triclabendazole-resistant *F. hepatica*. Inhibiting the efflux mechanism could allow the benzimidazole derivative to accumulate to toxic levels in the parasite.

In another embodiment, the invention comprises a composition comprising a benzimidazole compound in combination with a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridizine-3(2H)-one Examples of IGRs suitable for use include but are not limited to methoprene, pyriproxyfen, hydroprene, cyromazine, fluazuron, lufenuron, novaluron, pyrethroids, formamidines such as amitraz, 1-(2,6-difluorobenzoyl)-3-(2-fluoro-4-(trifluoromethyl)phenylurea, and novaluron.

In one embodiment, the compositions of the invention comprise a benzimidazole compound of formula (I), (II) or (III) in combination with methoprene and a pharmaceutically acceptable carrier.

In another embodiment, the IGR compound is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumoron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be added to the composition of the invention. These include pyrethrins (which include cinerin I, cinerin II, jasmolin I, jasmolin II, pyrethrin I, pyrethrin II and mixtures thereof) and pyrethroids, and carbamates (which include but are not limited to benomyl, carbanolate, carbaryl, carbofuran, meththiocarb, metolcarb, promacyl, propoxur, aldicarb, butocarboxim, oxamyl, thiocarboxime and thiofanox).

In some embodiments, the compositions of the invention may include one or more antinematodal agents including, but not limited to, active agents in the benzimidazoles, imidazothiazoles, tetrahydropyrimidines, organophosphates class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the compositions may include an imidazothiazole compounds including, but not limited to, tetramisole, levamisole and butamisole. In still other embodiments, the compositions of the invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the compositions may include the antinematodal compounds phenothiazine, piperazine as the neutral compound and in various salt forms, diethylcarbamazine, phenols such as disophenol, arsenicals such as arsenamide, ethanolamines such as bephenium, thenium closylate, and methyridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the compositions of the invention may include other antitrematodal agents. Suitable antitrematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalan, oxyclozanide, clioxanide, rafoxanide, brotianide, bromoxanide and closantel; triclabendazole, diamfenetide, clorsulon, hetolin and emetine.

Anticestodal compounds may also be advantageously used in the compositions of the invention including, but not limited to, arecoline in various salt forms, bunamidine, niclosamide, nitroscanate, paromomycin and paromomycin II.

In yet other embodiments, the compositions of the invention may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfuram, isobornyl thiocyanato acetate, methroprene, monosulfuram, pirenonylbutoxide, rotenone, triphenyltin acetate, triphenyltin hydroxide, deet, dimethyl phthalate, and the compounds 1,5a,6,9,9a,9b-hexahydro-4-a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

An antiparasitic agent that can be combined with the compounds of the invention to form a composition can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126(Pt 1):79-86).

An insecticidal agent that can be combined with the compounds of the invention to form a composition can be a substituted pyridylmethyl derivative compound such as imidacloprid. Agents of this class are described above, and for example, in U.S. Pat. No. 4,742,060 or in EP 0 892 060. It would be well within the skill level of the practitioner to decide which individual compound can be used in the inventive formulation to treat a particular infection of an insect.

In certain embodiments, an insecticidal agent that can be combined with the compositions of the invention is a semicarbazone, such as metaflumizone.

In another embodiment, the compositions of the invention may advantageously include one or more isoxazoline compounds known in the art. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the invention, nodulisporic acid and its derivatives (a class of known acaricidal, anthelminitic, anti-parasitic and insecticidal agents) may be added to the compositions of the invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the literature cited above.

In another embodiment, anthelmintic compounds of the amino acetonitrile class (AAD) of compounds such as monepantel (ZOLVIX) and the like may be added to the compositions of the invention. These compounds are described, for example, in WO 2004/024704; Sager et al., Veterinary Parasitology, 2009, 159, 49-54; Kaminsky et al., Nature vol. 452, 13 Mar. 2008, 176-181. The compositions of the invention may also include aryloazol-2-yl cyanoethylamino compounds such as those described in US 2008/0312272 to Soll et al., which is incorporated herein in its entirety, and thioamide derivatives of these compounds, as described in U.S. patent application Ser. No. 12/582,486, filed Oct. 20, 2009, which is incorporated herein by reference.

The compositions of the invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds are known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the formulations of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004,432, U.S. Pat. No. 5,703,078 and U.S. Pat. No. 5,750,695, all of which are hereby incorporated by reference in their entirety.

Dosage forms may contain from about 0.5 mg to about 5 g of a combination of active agents. In one embodiment of the dosage form, the amount of active is present in an amount of from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

Methods of Treatment

In another aspect, the invention is a method for treating helminth infestation comprising administration of an anthelmintically effective amount of a compound according to Formula (I), Formula (II) or Formula (III) to an animal in need thereof. In one embodiment, the helminths are trematodes. In another embodiment, the helminths are the liver fluke *Fasciola hepatica.*

In one embodiment of the invention, methods for the treatment or prevention of a parasitic infestation or infection in a domestic animal are provided, which comprise administering an oral, topical or injectable composition comprising an effective amount of at least one benzimidazole active agent to the animal. The compositions and methods of the invention are effective against endoparasites, trematodes in particular, of animals and humans.

In one embodiment, the invention provides methods for the treatment and prevention of parasitic infections and infestations of animals (either wild or domesticated), including livestock and companion animals such as cats, dogs, horses, sheep, goats, pigs and cattle, with the aim of ridding these hosts of liver flukes commonly encountered by such animals.

By "treating" or "treat" or "treatment" is intended the application or administration of a composition of the invention to an animal that has a parasitic infestation for the eradication of the parasite or the reduction of the number of the parasites infesting the animal undergoing treatment. It is noted that the compositions of the invention may be used to prevent such a parasitic infestation.

Additional Active Agents

Additional veterinary/pharmaceutical active ingredients may be used in accordance with all embodiments and aspects detailed above.

In general, the additional active agent is included in the composition in an amount of between about 0.1 μg and about 1000 mg. More typically, the additional active agent may be included in an amount of about 10 μg to about 500 mg, about 1 mg to about 300 mg, about 10 mg to about 200 mg or about 10 mg to about 100 mg.

In other embodiments of the invention, the additional active agent may be included in the composition to deliver a dose of about 5 μg/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 μg/kg to about 200 μg/kg or about 0.1 mg/kg to about 1 mg/kg of weight of animal. In still another embodiment of the invention, the additional active agent is included in a dose between about 0.5 mg/kg to about 50 mg/kg.

Optionally, a fragrance may be added to any of the compositions of the invention. Fragrances which are useful for the invention include but are not limited to:

(i) carboxylic acid esters such as octyl acetate, isoamyl acetate, isopropyl acetate and isobutyl acetate;

(ii) fragrant oils such as lavender oil.

The compositions of the invention are made by mixing the appropriate amount of the active agents, pharmaceutically acceptable carrier or diluent and optionally a crystallization inhibitor, antioxidant, preservative, film former, etc., to form a composition of the invention. In some embodiments the composition can be obtained by following the method of making these forms described above by the description of making these forms found in general formulation text known to those in the art, e.g., *Remington—The Science and Practice of Pharmacy* (*21st Edition*) (2005), *Goodman & Gilman's The Pharmacological Basis of Therapeutics* (*11th Edition*) (2005) and *Ansel's Pharmaceutical Dosage Forms and Drug Delivery Systems* (*8th Edition*), edited by Allen et al., Lippincott Williams & Wilkins, (2005).

The inventive formulations may contain other inert ingredients such as antioxidants, preservatives, or pH stabilizers. These compounds are well known in the formulation art. Antioxidants such as an alpha tocopherol, ascorbic acid, ascrobyl palmitate, fumaric acid, malic acid, sodium ascorbate, sodium metabisulfate, n-propyl gallate, BHA (butylated hydroxy anisole), BHT (butylated hydroxy toluene) monothioglycerol and the like, may be added to the present formulation. The antioxidants are generally added to the formulation in amounts of from about 0.01 to about 2.0%, based upon total weight of the formulation, such as about 0.05% to about 1.0%.

Preservatives, such as the parabens (methylparaben and/or propylparaben), are suitably used in the formulation in amounts ranging from about 0.01% to about 2.0%, or about 0.05% to about 1.0%. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Ranges for these compounds include from about 0.01% to about 5%.

Compounds which stabilize the pH of the formulation are also contemplated. Again, such compounds are well known to a practitioner in the art as well as how to use these compounds. Buffering systems include, for example, systems selected from the group consisting of acetic acid/acetate, malic acid/malate, citric acid/citrate, tataric acid/tartrate, lactic acid/lactate, phosphoric acid/phosphate, glycine/glycimate, tris, glutamic acid/glutamates or sodium carbonate.

The compositions of the invention are administered in parasiticidally effective amounts which are which are suitable to control the parasite in question to the desired extent, as described below. In each aspect of the invention, the compounds and compositions of the invention can be applied against a single pest or combinations thereof.

The compositions of the invention may be administered continuously, for treatment or prevention of parasitic infections or infestations. In this manner, the compositions of the invention deliver an effective amount of the active compounds to the animal in need thereof to control the target parasites. By "effective amount" is intended a sufficient amount of a composition of the invention to eradicate or reduce the number of parasites infesting the animal. In some embodiments, an effective amount of the active agent achieves at least 70% efficacy against the target parasite. In other embodiments, an effective amount of the active agent achieves at least 80%, or at least 90% efficacy against the target pests. In other embodiments, an effective amount of the active agent will achieve at least 95%, at least 98% or 100% efficacy against the target parasites.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

Higher amounts may be provided for very prolonged release in or on the body of the animal. In another treatment embodiment, the amount of active agents for animals which are small in size is greater than about 0.01 mg/kg, and in another embodiment for the treatment of small-sized animals the amount of active agents is between about 0.01 and about 20 mg/kg of weight of animal.

The solutions according to the invention may be applied using any means known per se, e.g., using an applicator gun or a metering flask, pipette, syringes, roll on, droppers, capsules, foil packages, vials, twist tip containers and other single dose and multi-dose containers.

In another aspect of the invention, a kit for the treatment or prevention of a parasitic infestation in an animal is provided, which comprises at least one isoxazoline active agent together with a pharmaceutically acceptable carrier and a dispensing device for topical application of the composition. The dispensing device may be a pipette, syringes, roll on, droppers, capsules, foil packages, vials, twist tip containers and other single dose and multi-dose containers, which includes an effective dose of each active agent in the pharmaceutically acceptable carrier or diluent.

An important aspect of the invention is to provide a multiple-use container comprising a topical composition of the invention, from which accurate single dose aliquots of the long lasting topical formulations may be administered. The formulation must remain stable with repetitive exposure to the outside environment, particularly oxygen and water. This embodiment may be particularly useful with the very long lasting formulations of the invention that require administration to an animal infrequently, such as once every 3-6 months, or similar. Some solvents such as ethers (including DMI and the like) give rise to peroxides, which then yield ketones and aldehydes that may be further degraded to acids. The presence of acids may contribute to the degradation of acid hydrolysis-susceptible molecules, including isoxazoline active agents. Thus, formulation stability is particularly important for the multi-dose container application, where the formulations can be exposed to oxygen and water during multiple rounds of opening and closing. Importantly, it was found that the use of certain antioxidants such as BHT and BHA efficiently inhibit the degradation of the active agent in ether solvents. For example, a 12% (w/v) solution of Compound A in DMI exhibited no significant change in assay over the course of an eleven week accelerated stability study at 50° C. in clear glass containers.

EXAMPLES

The invention is further described by the following non-limiting examples which further illustrate the invention and are not intended (nor should they be interpreted to) limit the scope of the invention. Compound examples of Formula (I) are listed first.

Compound number 130 (i.e., 6-chloro-5-(4-chlorophenyl)-2-trifluoromethylbenzimidazole was prepared as follows. A 250-mL round-bottom flask was purged and maintained with an inert atmosphere of nitrogen. 5-chloro-6-iodo-2-(trifluoromethyl)-1H-1,3-benzodiazole (400 mg, 1.15 mmol, 1.00 equiv), (4-chlorophenyl)boronic acid (359 mg, 2.30 mmol, 1.99 equiv), sodium carbonate (380 mg), dioxane (40 mL), $Pd(PPh_3)_4$ (67 mg), and water (10 mL) was placed in the flask. The resulting solution was stirred for 4 h at 100° C. in an oil bath. The mixture was cooled. The resulting solution was diluted with 100 mL of $H_2O$. The resulting solution was extracted with 3×100 mL of ethyl acetate and the organic layers combined. The resulting mixture was washed with 1×100 mL of brine (sat.). The combined organic layer was dried over anhydrous sodium sulfate and concentrated under vacuum. The residue was applied onto a silica gel column with ethyl acetate/petroleum ether (1:30). This resulted in 34.9 mg (9%) of 6-chloro-5-(4-chlorophenyl)-2-trifluoromethylbenzimidazole as a white solid.

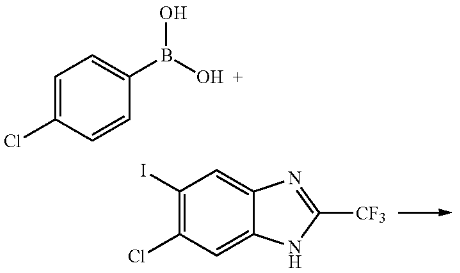

PH-MRL-209-043-3

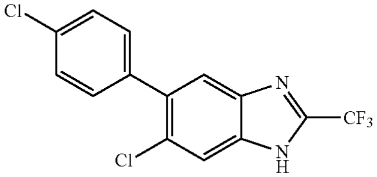

PH-MRL-209-130-0

Compound number 140 (i.e., 6-chloro-5-(2,3-dichlorophenoxy)-2-heptafluoropropylbenzimidazole) was prepared as follows. 4-chloro-5-(2,3-dichlorophenoxy)benzene-1,2-diamine (150 mg, 0.49 mmol, 1.00 equiv), heptafluorobutanoic acid (15 mL) and hydrogen chloride (3 mL) was placed into a 100-mL round-bottom flask. The resulting solution was stirred overnight at 110° C. in an oil bath. The reaction mixture was cooled to room temperature. The resulting solution was extracted with 3×50 mL of ethyl acetate and the organic layers combined. The resulting mixture was washed with 3×100 mL of brine. The resulting mixture was concentrated under vacuum. The residue was applied onto a silica gel column with ethyl acetate/petroleum ether (1:1). The crude product was re-crystallized from EA/hexane in the ratio of 1/1. This resulted in 63.4 mg (27%) of 6-chloro-5-(2,3-dichlorophenoxy)-2-heptafluoropropylbenzimidazole as a white solid.

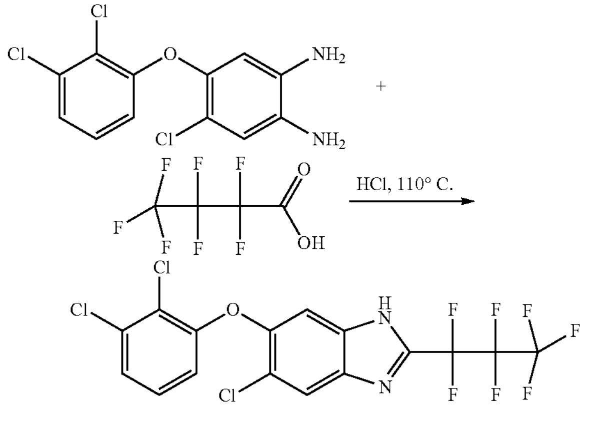

Compound number 247 (i.e., 6-chloro-5-(3,5-dichlorophenyl)-2-trifluoromethylbenzimidazole) was prepared as follows. A 100-mL round-bottom flask was purged and maintained with an inert atmosphere of nitrogen. 5-chloro-6-iodo-2-(trifluoromethyl)-1H-1,3-benzodiazole (200 mg, 0.58 mmol, 1.00 equiv), (3,5-dichlorophenyl)boronic acid (110 mg, 0.58 mmol, 2.00 equiv), dioxane (15 mL), $Pd(PPh_3)_4$ (66.8 mg, 0.06 mmol, 0.10 equiv), water (5 mL) and sodium methaneperoxoate sodium (183.8 mg, 1.72 mmol, 3.00 equiv) was placed in the flask. The resulting solution was stirred overnight at 100° C. in an oil bath. The reaction was then quenched by the addition of 15 mL of water. The resulting solution was extracted with 3×20 mL of ethyl acetate and the organic layers combined and dried over anhydrous sodium sulfate and concentrated under vacuum. The residue was applied onto a silica gel column with ethyl acetate/petroleum ether (1:10). The crude product (100 mg) was purified by Flash-Prep-HPLC with the following conditions (IntelFlash-2): Column, C18 silica gel; mobile phase, water increasing to acetonitrile within 40 min; Detector, UV 254 nm. 47.7 mg product was obtained. This resulted in 47.7 mg (23%) of 6-chloro-5-(3,5-dichlorophenyl)-2-trifluoromethylbenzimidazole as a white solid.

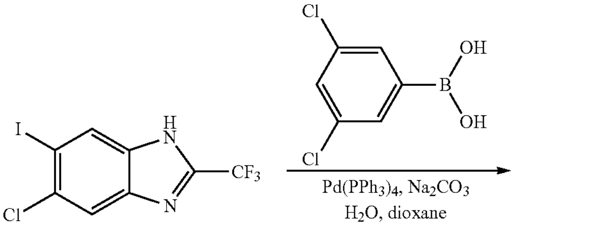

PH-MRL-209-043-3

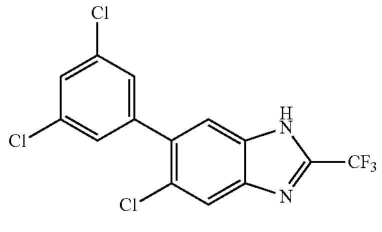

PH-MRL-209-247-0

Compound number 258 (i.e., 6-chloro-5-(3,4-dichlorophenyl)-2-trifluoromethylbenzimidazole) was prepared as follows. A 100-mL round-bottom flask was purged and maintained with an inert atmosphere of nitrogen. 5,6-dichloro-2-(trifluoromethyl)-1H-1,3-benzodiazole (200 mg, 0.78 mmol, 1.00 equiv), 1,4-dioxane (30 mL), (3,4-dichlorophenyl)boronic acid (229 mg, 1.20 mmol, 2.00 equiv), sodium carbonate (191 mg), water (8 mL) and $Pd(PPh_3)_4$ (34.7 mg) was placed into the flask. The resulting solution was stirred overnight at 100° C. in an oil bath. The resulting mixture was concentrated under vacuum. The residue was applied onto a silica gel column with ethyl acetate/petroleum ether (1:4). This resulted in 82.4 mg (29%) of 6-chloro-5-(3,4-dichlorophenyl)-2-trifluoromethylbenzimidazole as a white solid.

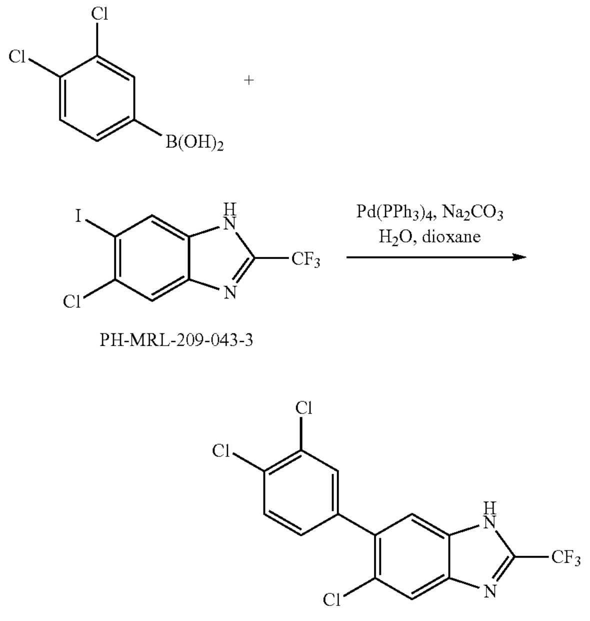

PH-MRL-209-043-3

PH-MRL-209-258-0

Compound number 260 (i.e., 6-chloro-5-(2,4-dichlorophenyl)-2-trifluoromethylbenzimidazole) was prepared as follows. A 100-mL round-bottom flask was purged and maintained with an inert atmosphere of nitrogen. (2,4-dichlorophenyl)boronic acid (229 mg, 1.20 mmol, 2.00 equiv), dioxane (30 mL), 5-chloro-6-iodo-2-(trifluoromethyl)-1H-1,3-benzodiazole (200 mg, 0.58 mmol, 1.00 equiv), sodium carbonate (191 mg), water (8 mL) and $Pd(PPh_3)_4$ (34.7 mg) was placed in the flask. The resulting solution was stirred overnight at 80° C. in an oil bath. The resulting mixture was concentrated under vacuum. The residue was applied onto a silica gel column with ethyl acetate/petroleum ether (1:4). This resulted in 87.8 mg (42%) of 6-chloro-5-(2,4-dichlorophenyl)-2-trifluoromethylbenzimidazole as a white solid.

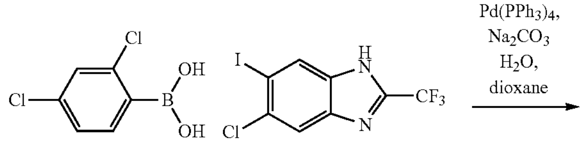

PH-MRL-209-258-3

-continued

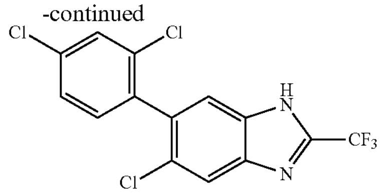

PH-MRL-209-260-0

Compound number 261 (i.e., 6-chloro-5-(2,3,5-trichlorophenyl)-2-trifluoromethylbenzimidazole) was prepared as follows. A 100-mL round-bottom flask purged and maintained with an inert atmosphere of nitrogen. (2,3,5-trichlorophenyl)boronic acid (284 mg, 1.26 mmol, 2.00 equiv), dioxane (30 mL), 5-chloro-6-iodo-2-(trifluoromethyl)-1H-1,3-benzodiazole (200 mg, 0.58 mmol, 1.00 equiv), sodium carbonate (191 mg), water (8 mL) and $Pd(PPh_3)_4$ (34.7 mg) was placed in the flask. The resulting solution was stirred overnight at 100° C. in an oil bath. The resulting mixture was concentrated under vacuum. The residue was applied onto a silica gel column with ethyl acetate/petroleum ether (1:4). This resulted in 22.3 mg (10%) of 6-chloro-5-(2,3,5-trichlorophenyl)-2-trifluoromethylbenzimidazole as a white solid.

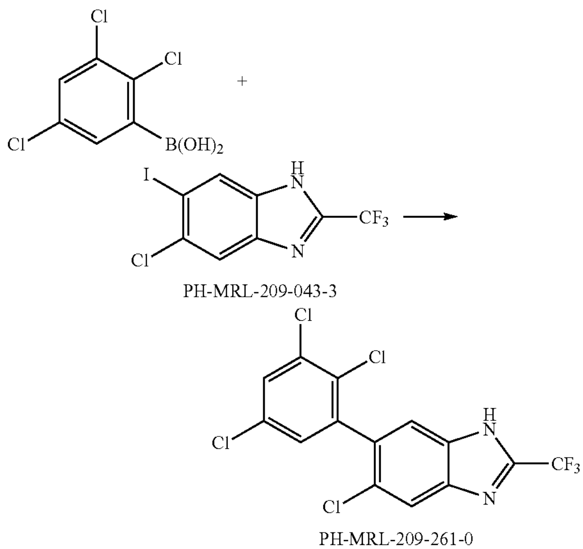

PH-MRL-209-043-3

PH-MRL-209-261-0

Compound examples of Formula (II) include compounds 14, 19, and 24.

Compound examples of Formula (III) include compounds 49, 102, 103 and 108.

Compound number 49 (i.e., 6-chloro-5-(2,3-dichlorophenoxy)-2-trifluoromethylthiobenzimidazole) was prepared as follows. A solution of 5-chloro-6-(2,3-dichlorophenoxy)-2,3-dihydro-1H-1,3-benzodiazole-2-thione (200 mg, 0.58 mmol, 1.00 equiv) in N,N-dimethylformamide (20 mL) and potassium carbonate (120 mg, 0.87 mmol, 1.50 equiv) was placed into a 50-mL 3-necked round-bottom flask. The mixture was sustained by aeration with trifluoro(iodo)methane. The resulting solution was stirred for 2 h at 130° C. in an oil bath. The resulting solution was diluted with 50 ml of water. The resulting solution was extracted with 2×80 ml of ethyl acetate and the organic layers combined. The resulting mixture was washed with 2×100 mL of brine. The mixture was dried over sodium sulfate and concentrated under vacuum.

The residue was applied onto a silica gel column with EA/PE (1:15). This resulted in 81.0 mg (34%) of 6-chloro-5-(2,3-dichlorophenoxy)-2-trifluoromethylthiobenzimidazole as an off-white solid.

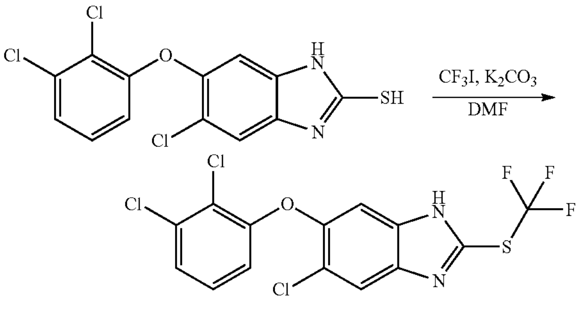

PH-MRL-209-049-0

Compound number 102 (i.e., 6-chloro-5-(4-chlorophenyl)-2-trifluoromethylthiobenzimidazole) was prepared as follows. A 250-mL 3-necked round-bottom flask was charged with a solution of 5-chloro-6-iodo-2,3-dihydro-1H-1,3-benzodiazole-2-thione (2 g, 6.44 mmol, 1.00 equiv) in N,N-dimethylformamide (100 mL) and potassium hydroxide (1.1 g, 3.00 equiv). Trifluoro(iodo)methane was introduced to the above. The resulting solution was stirred for 3 h at 120° C. in an oil bath. The resulting solution was diluted with 250 mL of ethyl acetate. The resulting mixture was washed with 3×200 mL of water and 2×200 mL of brine. The resulting mixture was concentrated under vacuum. The residue was applied onto a silica gel column with ethyl acetate/petroleum ether (1:10). This resulted in 400 mg (16%) of 5-chloro-6-iodo-2-[(trifluoromethyl)sulfanyl]-1H-1,3-benzodiazole as a yellow solid.

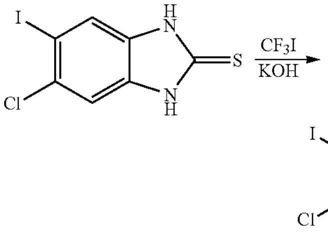

PH-MRL-209-102-4

Next, a 100-mL 3-necked round-bottom flask was purged and maintained with an inert atmosphere of nitrogen. 5-chloro-6-iodo-2-[(trifluoromethyl)sulfanyl]-1H-1,3-benzodiazole (400 mg, 1.06 mmol, 1.00 equiv), (4-chlorophenyl)boronic acid (330 mg, 2.11 mmol, 2.00 equiv), $Pd(PPh_3)_4$ (61 mg, 0.05 mmol, 0.05 equiv), $Na_2CO_3$ (336 mg, 3.14 mmol, 3.00 equiv), dioxane (40 mL) and water (10 mL) was placed into the flask. The resulting solution was stirred overnight at 100° C. in an oil bath. The reaction mixture was cooled to room temperature. The resulting solution was diluted with 200 mL of water. The resulting solution was extracted with 3×200 mL of ethyl acetate and the organic layers combined. The resulting mixture was washed with 2×200 mL of brine. The mixture was dried over anhydrous sodium sulfate and concentrated under vacuum. The crude product (200 mg) was purified by Flash-Prep-HPLC with the following conditions (CombiFlash-1): Column, C18 silica gel; mobile phase, $CH_3CN$/water=10:100 increasing to $CH_3CN$/water=100:0 within 35 min; Detector, UV 254 nm. 80 mg product was obtained. This resulted in 80 mg (21%) of 6-chloro-5-(4-chlorophenyl)-2-trifluoromethylthiobenzimidazole as an off-white solid.

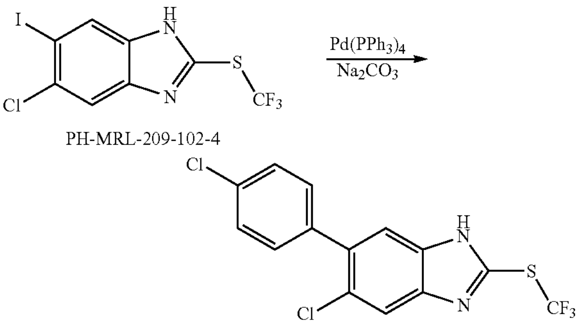

PH-MRL-209-102-4

PH-MRL-209-102-0

Compound number 103 (i.e., 6-chloro-5-(3-chlorophenyl)-2-trifluoromethylthiobenzimidazole) was prepared as follows. A 50-mL round-bottom flask was purged and maintained with an inert atmosphere of nitrogen. 5-chloro-2-nitroaniline (10 g, 57.95 mmol, 1.00 equiv), acetic acid (100 mL) and NIS (13 g, 57.78 mmol, 1.00 equiv) was placed in the flask. The resulting solution was stirred for 3 h at 50° C. in an oil bath. The resulting solution was poured into 300 mL of $H_2O$. The solid was collected by filtration. The solid was washed with 200 mL of (sat.) sodium bicarbonate and 3×200 mL of $H_2O$. This resulted in 17 g (88%) of 5-chloro-4-iodo-2-nitroaniline as a yellow solid.

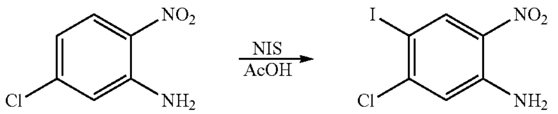

Next, a solution of 5-chloro-4-iodo-2-nitroaniline (15 g, 50.26 mmol, 1.00 equiv) in ethanol/$H_2O$ (400/50 mL), Fe powder (16.9 g, 301.79 mmol, 6.00 equiv) and $NH_4Cl$ (8 g, 149.53 mmol, 3.00 equiv) was placed into a 1000-mL round-bottom flask. The resulting solution was stirred for 2 h at 70° C. The resulting mixture was concentrated under vacuum. The resulting solution was extracted with 3×500 mL of ethyl acetate and the organic layers combined. The resulting mixture was washed with 3×100 mL of brine, dried and concentrated under vacuum. This resulted in 10 g (74%) of 4-chloro-5-iodobenzene-1,2-diamine as a black solid.

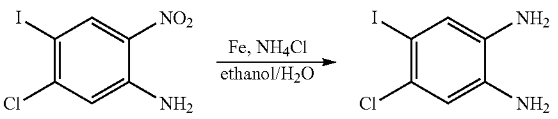

From this, a 100-mL round-bottom flask purged and maintained with an inert atmosphere of nitrogen. A solution of 4-chloro-5-iodobenzene-1,2-diamine (2.69 g, 10.02 mmol, 1.00 equiv) in ethanol (50 mL), $CS_2$ (6 g, 78.95 mmol, 8.00 equiv) and potassium hydroxide (1.68 g, 30.00 mmol, 3.00 equiv) was placed into the flask. The resulting solution was heated to reflux for 3 h. The resulting mixture was concentrated under vacuum. The resulting solution was diluted with 100 mL of $H_2O$. The resulting solution was extracted with 3×100 mL of ethyl acetate and the organic layers combined. The resulting mixture was washed with 100 mL of brine. The mixture was dried over anhydrous sodium sulfate and concentrated under vacuum. This resulted in 2.5 g (80%) of 5-chloro-6-iodo-2,3-dihydro-1H-1,3-benzodiazole-2-thione as a brown solid.

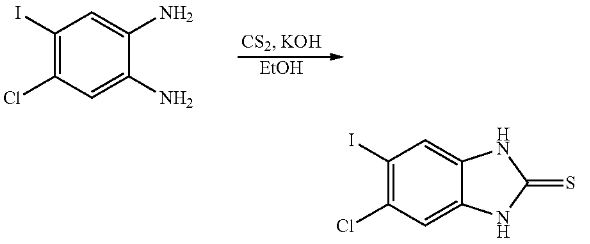

Next, a solution of 5-chloro-6-iodo-2,3-dihydro-1H-1,3-benzodiazole-2-thione (600 mg, 1.93 mmol, 1.00 equiv) in N,N-dimethylformamide (50 mL) and potassium hydroxide (325 mg, 5.80 mmol, 3.00 equiv) was placed into a 100-mL sealed tube. $CF_3I$(g) was then introduced. The resulting solution was stirred overnight at 80° C. The resulting solution was diluted with 250 mL of $H_2O$. The resulting solution was extracted with 3×300 mL of ethyl acetate and the organic layers combined. The resulting mixture was washed with 100 mL of brine. The mixture was dried over sodium sulfate and concentrated under vacuum. The residue was applied onto a silica gel column with ethyl acetate/petroleum ether (1/1). This resulted in 240 mg (33%) of 5-chloro-6-iodo-2-[(trifluoromethyl)sulfanyl]-1H-1,3-benzodiazole as a yellow solid.

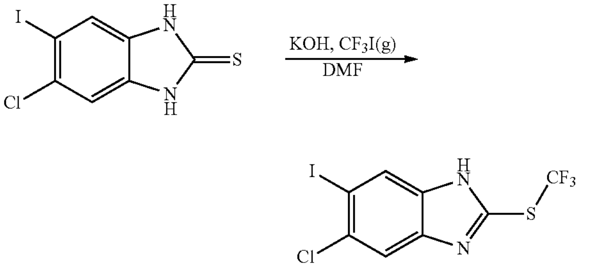

Finally, a 50-mL round-bottom flask purged and maintained with an inert atmosphere of nitrogen. 5-chloro-6-iodo-2-[(trifluoromethyl)sulfanyl]-1H-1,3-benzodiazole (240 mg, 0.63 mmol, 1.00 equiv), (3-chlorophenyl)boronic acid (150 mg, 0.96 mmol, 1.50 equiv), potassium carbonate (4 mL, 2 N aqueous solution), toluene (10 mL) and ethanol (0.5 mL) was placed into the flask. The resulting solution was stirred overnight at 100° C. The resulting solution was diluted with 100 mL of ethyl acetate. The resulting mixture was washed with 100 mL of brine. The mixture was dried over anhydrous sodium sulfate and concentrated under vacuum. The residue was applied onto a silica gel column with ethyl acetate/petroleum ether (1/1). This resulted in 73.3 mg (32%) of 6-chloro-5-(3-chlorophenyl)-2-trifluoromethylthiobenzimidazole as a off-white solid.

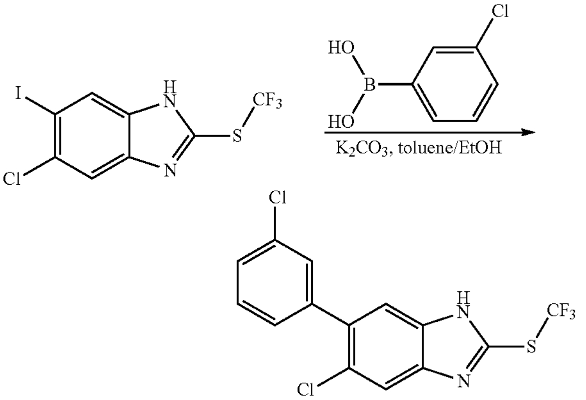

Compound number 108 (i.e., 6-chloro-5-(2-butyl)-cyclopropyl-2-trifluoromethylthiobenzimidazole) was prepared as follows. A 100-mL 3-necked round-bottom flask was purged and maintained with an inert atmosphere of nitrogen. A solution of $Et_2Zn$ (2 mL) in dichloromethane (2 mL) was placed into the flask. A solution of trifluoroacetic acid (0.15 mL) in dichloromethane (1 mL) at 0° C. was added dropwise. Next, a solution of $CH_2I_2$ (0.16 mL) in dichloromethane (1 mL) at 0° C. was added dropwise. Next, a solution of 5-chloro-6-[(1Z)-hex-1-en-1-yl]-2-[(trifluoromethyl)sulfanyl]-1H-1,3-benzodiazole (336 mg, 1.00 mmol, 1.00 equiv) in dichloromethane (1 mL) at 0° C. was added dropwise. The resulting solution was stirred for 3 h at room temperature. The resulting mixture was concentrated under vacuum. The residue was dissolved in 100 mL of $H_2O$/ethyl acetate (1:1). The resulting solution was extracted with 2×50 mL of ethyl acetate and the organic layers combined. The combined organic layer was dried over anhydrous sodium sulfate and concentrated under vacuum. The residue was applied onto a silica gel column with ethyl acetate and purification with EA/PE (1:20). This resulted in 14.9 mg (4%) of 6-chloro-5-(2-butyl)-cyclopropyl-2-trifluoromethylthiobenzimidazole as an off-white solid.

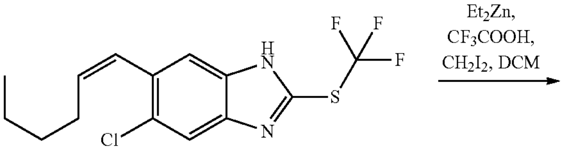

PH-MRL-209-106-0

PH-MRL-209-108-0

Compound number 262-100 was prepared as follows.

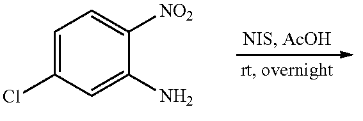

-continued

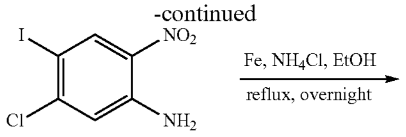

PH-MRL-209-262-1

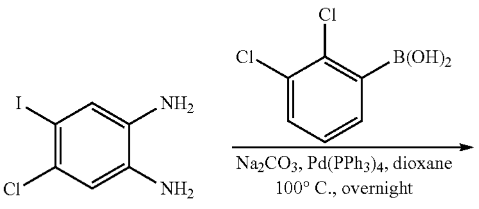

PH-MRL-209-262-2

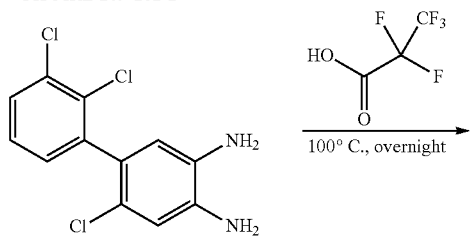

PH-MRL-209-262-4

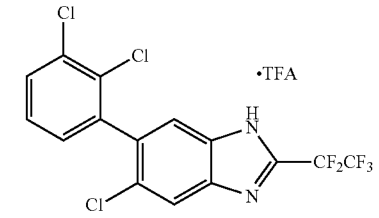

PH-MRL-209-262-0

To a solution of 5-chloro-2-nitroaniline (500 mg, 2.90 mmol) in acetic acid (20 ml) was added NIS (650 mg, 2.89 mmol). The resulting solution was stirred overnight at room temperature and then diluted with water (40 ml). The solids were collected by filtration to afford 5-chloro-4-iodo-2-nitroaniline as a brown solid (800 mg, crude). To a solution of 5-chloro-4-iodo-2-nitroaniline (800 mg, crude) in water (4 ml) and ethanol (20 ml) was added Fe powder (600 mg, 10.74 mmol) and ammonium chloride (430 mg, 8.04 mmol). The resulting solution was stirred overnight at reflux and then cooled to room temperature. The solid was filtered out and the filtrate was concentrated under vacuum. The residue was dissolved in ethyl acetate (200 ml) and washed with brine (100 ml), dried over $Na_2SO_4$ and concentrated under vacuum to afford 4-chloro-5-iodobenzene-1,2-diamine as a brown solid (600 mg, crude).

To a solution of 4-chloro-5-iodobenzene-1,2-diamine (100 mg, 0.37 mmol) in dioxane (15 ml) and water (5 ml) was added (2,3-dichlorophenyl)boronic acid (141.3 mg, 0.74 mmol), sodium carbonate (118.2 mg, 1.10 mmol) and $Pd(PPh_3)_4$ (42.9 mg, 0.04 mmol). The resulting solution was stirred overnight at 100° C. within an inert atmosphere of nitrogen. The resulting solution was concentrated under vacuum and dissolved in water (100 ml) and extracted with ethyl acetate (4×30 ml). The combined organic layers were dried over anhydrous sodium sulfate and concentrated under vacuum to give a residue, which was purified by a silica gel column with between 5% to 25% ethyl acetate in petroleum ether to afford 4-chloro-5-(2,3-dichlorophenyl)benzene-1,2-diamine as a brown solid (92 mg, crude). Finally, the solution of 4-chloro-5-(2,3-dichlorophenyl)benzene-1,2-diamine (100 mg, 0.35 mmol) in pentafluoropropionic acid (35 ml) and hydrochloric acid (conc, 7 ml) was stirred overnight at 100° C. and then concentrated under vacuum. The residue was dissolved in water (100 ml) and extracted with ethyl acetate (4×30 ml), dried over anhydrous sodium sulfate and concentrated. The crude product (500 mg) was purified by Prep-HPLC to afford 5-chloro-6-(2,3-dichlorophenyl)-2-(pentafluoroethyl)-1H-1,3-benzodiazole. TFA salt as a white solid (42 mg).

Compound number 263-100 was prepared as follows.

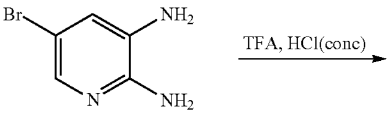

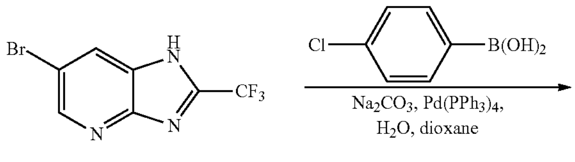

PH-MRL-209-263-1

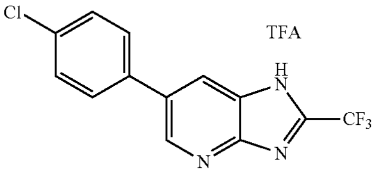

PH-MRL-209-263-100

A solution of 5-bromopyridine-2,3-diamine (100 mg, 0.53 mmol) in trifluoroacetic acid (20 mL) and hydrochloric acid (4 mL) was stirred overnight at 80° C. in an oil bath. The resulting mixture was concentrated under vacuum and dissolved in water (100 ml), adjusted to pH 8 with sodium carbonate and extracted with ethyl acetate (3×80 ml). The combined organic layers were dried over anhydrous magnesium sulfate and concentrated under vacuum to produce 6-bromo-2-(trifluoromethyl)-1H-imidazo[4,5-b]pyridine as a brown solid (200 mg, crude). To a solution of (4-chlorophenyl)boronic acid (117 mg, 0.75 mmol) in water (5 mL) and dioxane (15 mL) was added 6-bromo-2-(trifluoromethyl)-1H-imidazo[4,5-b]pyridine (100 mg, crude), $Pd(PPh_3)_4$ (43.4 mg, 0.04 mmol) and sodium carbonate (119.5 mg, 1.13 mmol). The resulting solution was stirred overnight at 100° C. with an inert atmosphere of nitrogen and then concentrated under vacuum. The residue was dissolved in water (50 mL), extracted with ethyl acetate (4×50 mL), the organic layers combined and dried over anhydrous sodium sulfate and concentrated under vacuum. The crude product (60 mg) was purified by Prep-HPLC to produce 6-(4-chlorophenyl)-2-(trifluoromethyl)-1H-imidazo[4,5-b]pyridine. TFA salt as a white solid (30 mg).

Compound number 264-100 was prepared as follows.

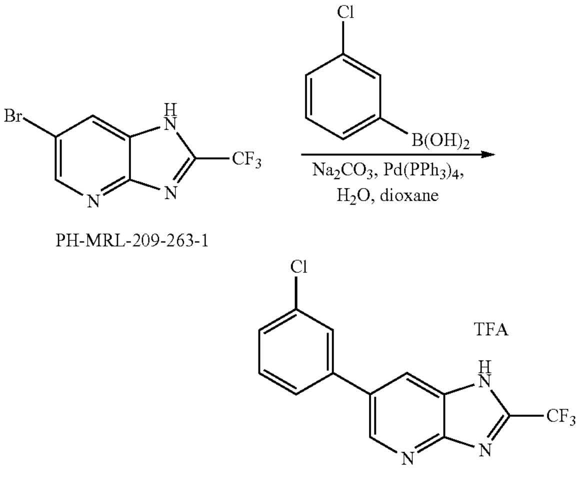

PH-MRL-209-263-1

PH-MRL-209-264-100

To a solution of (3-chlorophenyl)boronic acid (117 mg, 0.75 mmol) in water (5 mL) and dioxane (15 mL) was added 6-bromo-2-(trifluoromethyl)-1H-imidazo[4,5-b]pyridine (100 mg, crude), $Pd(PPh_3)_4$ (43.4 mg, 0.04 mmol) and sodium carbonate (119.5 mg, 1.13 mmol). The resulting solution was stirred overnight at 100° C. with an inert atmosphere of nitrogen and then concentrated under vacuum. The residue was dissolved in water (50 mL), extracted with ethyl acetate (4×50 mL), the organic layers combined and dried over anhydrous sodium sulfate and concentrated under vacuum. The crude product (60 mg) was purified by Prep-HPLC to produce 6-(3-chlorophenyl)-2-(trifluoromethyl)-1H-imidazo[4,5-b]pyridine. TFA salt as a white solid (42 mg).

The compound 265-100 was prepared as follows.

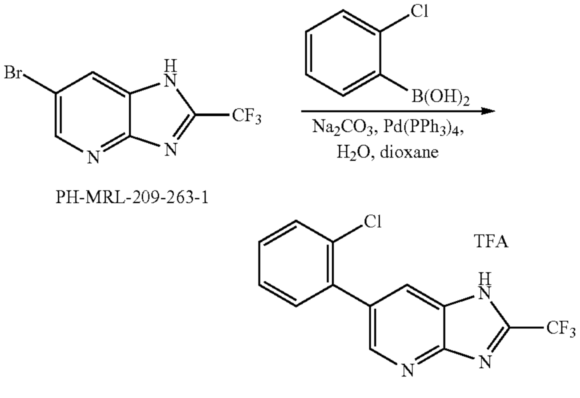

PH-MRL-209-263-1

PH-MRL-209-265-100

To a solution of (2-chlorophenyl)boronic acid (117 mg, 0.75 mmol) in water (5 mL) and dioxane (15 mL) was added 6-bromo-2-(trifluoromethyl)-1H-imidazo[4,5-b]pyridine (100 mg, crude), $Pd(PPh_3)_4$ (43.4 mg, 0.04 mmol) and sodium carbonate (119.5 mg, 1.13 mmol). The resulting solution was stirred overnight at 100° C. with an inert atmosphere of nitrogen and then concentrated under vacuum. The residue was dissolved in water (50 mL), extracted with ethyl acetate (4×50 mL) and the organic layers combined and dried over anhydrous sodium sulfate and concentrated under vacuum. The crude product (60 mg) was purified by Prep-HPLC to make 6-(2-chlorophenyl)-2-(trifluoromethyl)-1H-imidazo[4,5-b]pyridine. TFA salt as a white solid (20 mg).

Compound number 266-100 was prepared as follows.

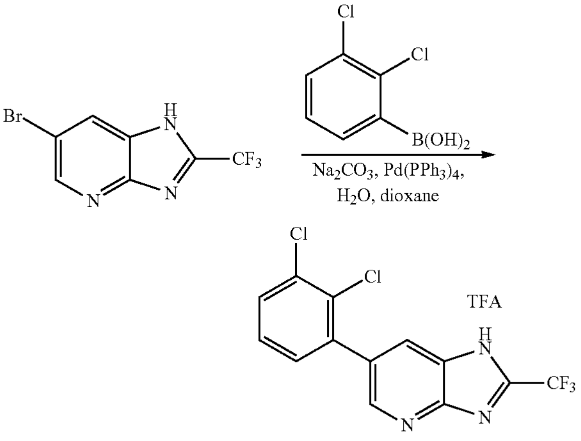

PH-MRL-209-266-100

To a solution of (2,3-chlorophenyl)boronic acid (143 mg, 0.75 mmol) in water (5 mL) and dioxane (15 mL) was added 6-bromo-2-(trifluoromethyl)-1H-imidazo[4,5-b]pyridine (100 mg, crude), $Pd(PPh_3)_4$ (43.4 mg, 0.04 mmol) and sodium carbonate (120 mg, 1.13 mmol). The resulting solution was stirred overnight at 100° C. with an inert atmosphere of nitrogen and then concentrated under vacuum. The residue was dissolved in water (50 mL), extracted with ethyl acetate (4×50 mL) and the organic layers combined and dried over anhydrous sodium sulfate and concentrated under vacuum. The crude product was purified by Prep-HPLC to afford 6-(2,3-chlorophenyl)-2-(trifluoromethyl)-1H-imidazo[4,5-b]pyridine. TFA salt as a white solid (35.7 mg).

The compound 268-100 was prepared as follows.

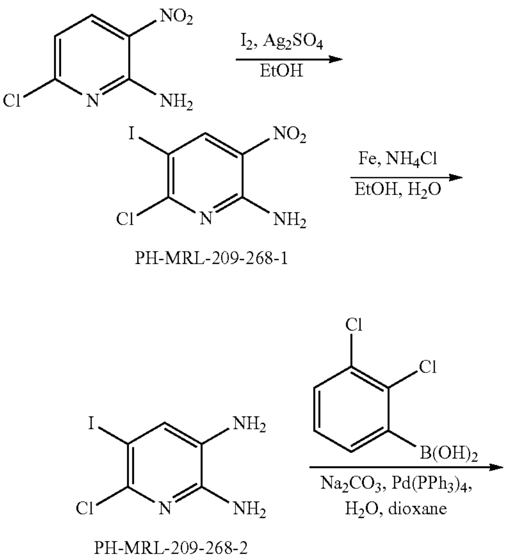

PH-MRL-209-268-1

PH-MRL-209-268-2

-continued

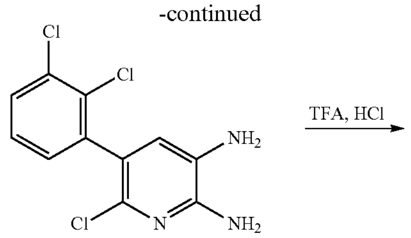

PH-MRL-209-268-3

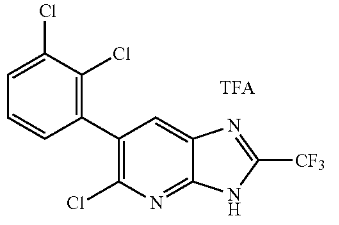

PH-MRL-209-268-100

To a solution of 6-chloro-3-nitropyridin-2-amine (630 mg, 3.63 mmol) in ethanol (11 mL) was add $I_2$ (920 mg, 3.62 mmol) and $Ag_2SO_4$ (1132 mg, 3.63 mmol).). The resulting solution was stirred overnight at room temperature and dissolved in water (100 mL), then extracted with ethyl acetate (3×80 ml). The combined organic layers were washed with brine (50 ml), dried over anhydrous sodium sulfate and concentrated under vacuum to produce 6-chloro-5-iodo-3-nitropyridin-2-amine as a yellow solid (640 mg, 59%). Next, to a solution of 6-chloro-5-iodo-3-nitropyridin-2-amine (640 mg, 2.14 mmol) in ethanol (40 ml) and water (10 ml) was added Fe powder (1.93 g, 34.46 mmol) and $NH_4Cl$ (887 mg, 16.58 mmol). The resulting solution was heated to reflux for 4 h and then concentrated. The residue was dissolved in water (100 mL) and extracted with ethyl acetate (3×80 ml). The combined organic layers was washed with brine (50 mL), dried over anhydrous sodium sulfate and concentrated under vacuum. The residue was purified by a silica gel column with 33% ethyl acetate in petroleum ether to produce 6-chloro-5-iodopyridine-2,3-diamine as a brown solid (560 mg, 97%). The mixture of 6-chloro-5-iodopyridine-2,3-diamine (100 mg, 0.37 mmol), (2,3-dichlorophenyl)boronic acid (147.3 mg, 0.77 mmol), $Pd(Ph_3P)_4$ (42.9 mg, 0.04 mmol) and sodium carbonate (118.2 mg, 1.12 mmol) in water (5 mL) and dioxane (15 mL) was heated to reflux overnight. Then the resulting solution was quenched with water (100 mL) and extracted with ethyl acetate (3×50 ml). The combined organic layers were washed with brine (50 mL), dried over anhydrous sodium sulfate and concentrated under vacuum. The residue was purified by a silica gel column with 50% ethyl acetate in petroleum ether to produce 6-chloro-5-(2,3-dichlorophenyl) pyridine-2,3-diamine as a brown solid (80 mg, 75%). Finally, the solution of 6-chloro-5-(2,3-dichlorophenyl)pyridine-2,3-diamine (80 mg, 0.28 mmol) in trifluoroacetic acid (10 mL) and hydrochloric acid (conc., 2 mL) was heated to reflux overnight. Then the resulting mixture was quenched with water (100 mL), adjusted pH to 8 with sodium carbonate and extracted with ethyl acetate (3×80 mL). The combined organic layers was dried over anhydrous magnesium sulfate and concentrated to give a residue, which was purified by a silica gel column with 50% ethyl acetate in petroleum ether to produce 5-chloro-6-(2,3-dichlorophenyl)-2-(trifluoromethyl)-1H-imidazo[4,5-b]pyridine. Trifluoroacetic acid as a off-white solid (2 mg, 2%).

The compound number 273 was prepared as follows.

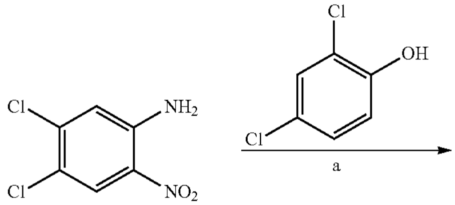

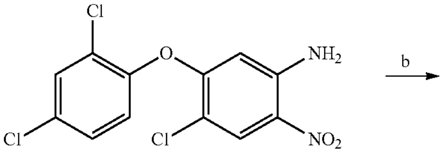

PH-MRL-209-273-1

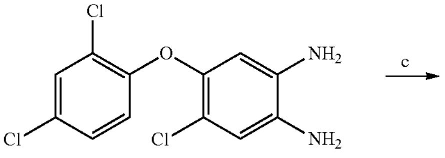

PH-MRL-209-273-2

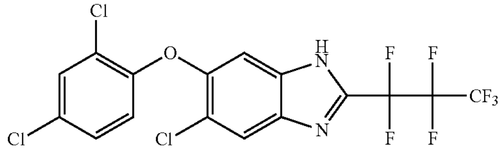

PH-MRL-209-273-0

Reagents and conditions: (a) $K_2CO_3$, DMSO, 90° C., overnight, 71%;
(b) Zn, HCl (conc), EtOH, rt~reflux, 4 h, 75%;
(c) Heptafluorobutyric Acid as solvent, 80° C., overnight, 47%.

To a solution of 4,5-dichloro-2-nitroaniline (20 g, 96.61 mmol) in DMSO (200 ml) was added 2,4-dichlorophenol (15.8 g, 96.93 mmol) and potassium carbonate (26.7 g, 193.18 mmol). The resulting solution was stirred overnight at 90° C. and then quenched by the addition of water (1000 ml). The resulting solution was extracted with ethyl acetate (3×500 ml) and the organic layers combined and dried over anhydrous magnesium sulfate. The solids were filtered out. The resulting mixture was concentrated under vacuum to give a residue, which was purified by a silica gel column with 10%~20% ethyl acetate in petroleum ether to produce 4-chloro-5-(2,4-dichlorophenoxy)-2-nitroaniline as a yellow solid (23 g, 71%). Next, the 4-chloro-5-(2,4-dichlorophenoxy)-2-nitroaniline (22 g, 65.96 mmol) was added to ethanol (200 ml) and hydrogen chloride (16 ml, 197.9 mmol). This was followed by the addition of Zn powder (21.4 g, 395.8 mmol) at room temperature in portions. The resulting solution was stirred for 4 h at 85° C. and then concentrated under vacuum. The residue was dissolved in water (500 ml), adjusted pH to 8 with aqueous sodium bicarbonate and extracted with ethyl acetate (4×200 ml). The combined organic layers were dried and concentrated under reduce pressure to give a residue, which was purified by a silica gel column with 10%~20% ethyl acetate in petroleum ether to afford 4-chloro-5-(2,4-dichlorophenoxy)benzene-1,2-diamine as a red oil (15 g, 75%). Finally, a solution of 4-chloro-5-(2,4-dichlorophenoxy)benzene-1,2-diamine (14 g, 46.12 mmol) in heptafluorobutanoic acid (150 ml) was stirred overnight at 80° C. in an oil bath. The reaction was then quenched by the addition of water (400 ml), adjusted pH value of the solution to 7 with aqueous sodium bicarbonate and extracted with ethyl acetate (3×200 ml). The combined organic layers were dried over anhydrous magnesium sulfate and concentrated under reduced pressure to give a residue, which was purified by a silica gel column with 2%~10% ethyl acetate in petroleum ether to produce 5-chloro-6-(2,4-dichlorophenoxy)-2-(heptafluoropropyl)-1H-1,3-benzodiazole as a white solid (10.4705 g, 47%).

The compound number 274 was prepared as follows.

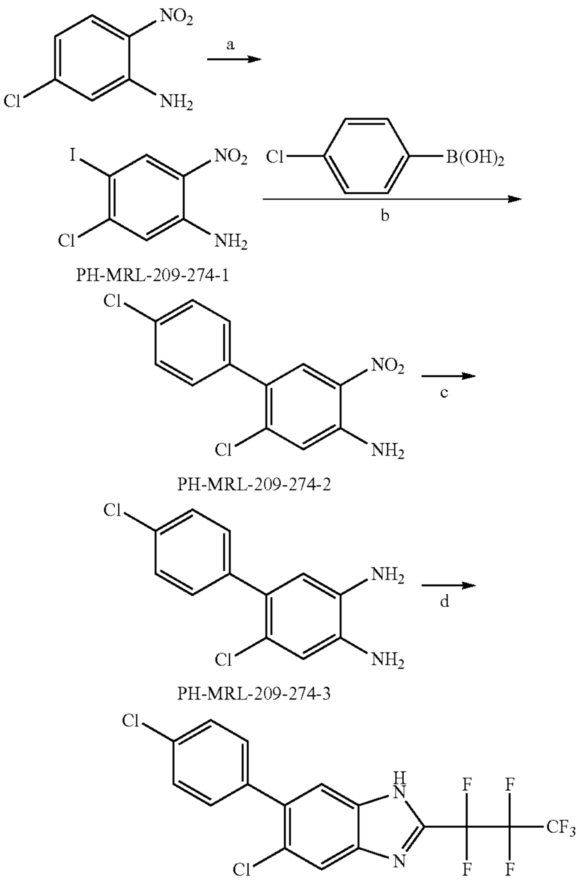

PH-MRL-209-274-1

PH-MRL-209-274-2

PH-MRL-209-274-3

PH-MRL-209-274-0

Reagents and conditions: (a) NIS, AcOH, rt, overnight, 81%; (b) $K_3PO_4$, $Pd(PPh_3)_4$, $H_2O$, dioxane, 95° C., 6 h, 63%; (c) Zn, HCl (conc), EtOH, reflux, 4 h, 81%; (d) heptafluorobutanoic acid, 120° C., 1.5 h, 62%

To a solution of 5-chloro-2-nitroaniline (50 g, 289.74 mmol) in AcOH (200 ml) was added NIS (63 g, 280.02 mmol) with stirring overnight at room temperature. Then the solids were collected by filtration and washed with water (50 ml). The solid was dried in an oven under reduced pressure to afford 5-chloro-4-iodo-2-nitroaniline as a yellow solid (70 g, 81%). Next, to a solution of 5-chloro-4-iodo-2-nitroaniline (15 g, 50.26 mmol) in dioxane (200 ml) and water (20 ml) was added (4-chlorophenyl)boronic acid (15.7 g, 100.40 mmol), $K_3PO_4$ (21.2 g, 99.87 mmol) and $Pd(PPh_3)_4$ (3 g, 2.60 mmol) with stirring for 6 h at 95° C. maintained with an inert atmosphere of nitrogen. Then the resulting mixture was concentrated under vacuum to give a residue, which was purified by a silica gel column with 5%~10% ethyl acetate in petroleum ether to afford 5-chloro-4-(4-chlorophenyl)-2-nitroaniline as a yellow solid (9 g, 63%). To a solution of 5-chloro-4-(4-chlorophenyl)-2-nitroaniline (12 g, 42.39 mmol) in ethanol (150 ml) was added hydrogen chloride (conc, 10 ml) to this was followed by the addition of Zn powder (16.6 g, 253.34 mmol) in portions at room temperature. The resulting solution was stirred for 4 h at 85° C. Then the resulting mixture was concentrated under vacuum, dissolved in water (200 ml) and extracted with ethyl acetate (3×200 ml). The combined organic layers was dried and concentrated under vacuum to give a residue, which was purified by a silica gel column with 10%~20% ethyl acetate in petroleum ether to produce 4-chloro-5-(4-chlorophenyl)benzene-1,2-diamine as an off-white solid (8.7 g, 81%). Finally, a solution of 4-chloro-5-(4-chlorophenyl)benzene-1,2-diamine (7 g, 27.65 mmol) in heptafluorobutanoic acid (70 ml) was stirred for 1.5 h at 120° C. Then the mixture was poured into water (200 ml), adjusted pH value of the solution to 7 with aqueous sodium bicarbonate and extracted with ethyl acetate (3×200 ml). The combined organic layers was dried over anhydrous magnesium sulfate and concentrated under vacuum to give a residue, which was purified by a silica gel column with 5% ethyl acetate in petroleum ether to afford 5-chloro-6-(4-chlorophenyl)-2-(heptafluoropropyl)-1H-1,3-benzodiazole as an off-white solid (7.3977 g, 62%).

Compound number 275 was prepared as follows.

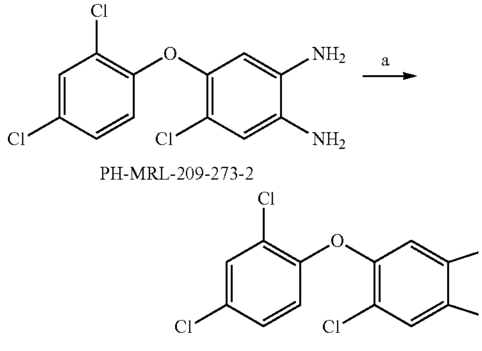

PH-MRL-209-273-2

PH-MRL-209-275-0

Reagents and conditions: (a) TFA, HCl (conc), 80° C., overnight, 66%

A solution of 4-chloro-5-(2,4-dichlorophenoxy)benzene-1,2-diamine (100 mg, 0.33 mmol) in trifluoroacetic acid (5 ml) and hydrogen chloride (conc. 1 ml) was stirred overnight at 80° C. The reaction was then quenched water (100 ml), extracted with ethyl acetate (2×50 ml) and the organic layers combined. The resulting mixture was washed with saturated aqueous $NaHCO_3$ (100 ml), dried over anhydrous sodium sulfate and concentrated under reduce pressure to give a residue, which was purified by a silica gel column with 5%~10% ethyl acetate in petroleum ether to produce 5-chloro-6-(2,4-dichlorophenoxy)-2-(trifluoromethyl)-1H-1,3-benzodiazole as a white solid (82.4 mg, 66%).

Compound number 276 was prepared as follows.

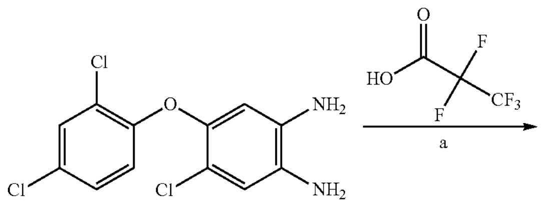

PH-MRL-209-273-2

-continued

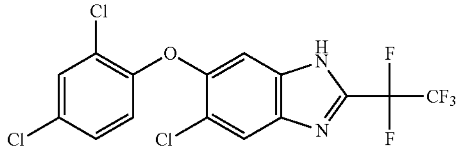

PH-MRL-209-276-0

Reagents and conditions: (a) 80° C., overnight, 15%

A solution of 4-chloro-5-(2,4-dichlorophenoxy)benzene-1,2-diamine (100 mg, 0.33 mmol) in pentafluoropropanoic acid (5 ml) was stirred overnight at 80° C. in an oil bath. The reaction was then quenched by the addition of water (20 ml), adjusted to pH 7 with aqueous sodium bicarbonate and extracted with ethyl acetate (2×50 ml). The combined organic layers were dried over anhydrous magnesium sulfate and concentrated under vacuum to give a residue which was purified by Pre-TLC with 10% ethyl acetate in petroleum ether to produce 5-chloro-6-(2,4-dichlorophenoxy)-2-(pentafluoroethyl)-1H-1,3-benzodiazole as a white solid (21.4 mg, 15%).

Compound number 277 was prepared as follows.

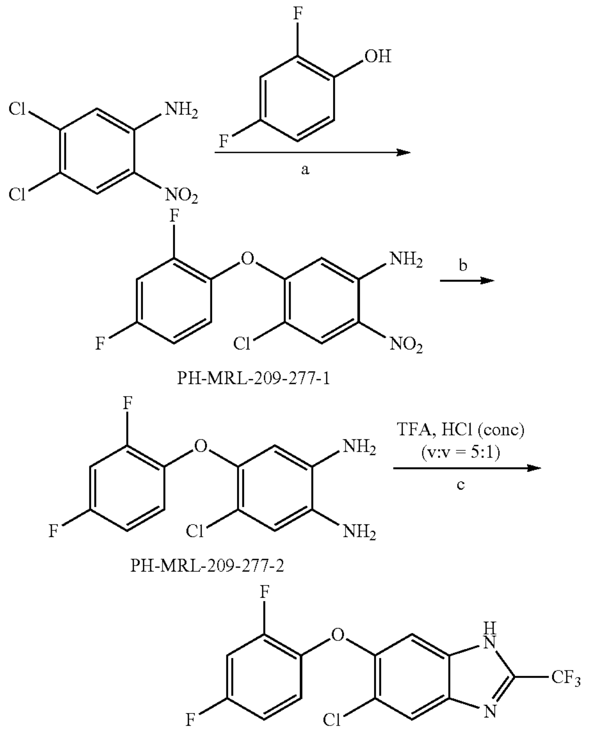

PH-MRL-209-277-0

Reagents and conditions: (a) $K_2CO_3$, DMSO, 90° C., overnight, 30%; (b) Zn, HCl (conc), EtOH, rt~reflux 4 h, 51%; (c) 80° C., overnight, 57%.

To a solution of 2,4-difluorophenol (1.9 g, 14.61 mmol) in DMSO (20 ml) was added 4,5-dichloro-2-nitroaniline (3 g, 14.49 mmol) and potassium carbonate (4 g, 28.94 mmol) with stirring overnight at 90° C. Then the reaction was quenched with water (200 ml) and extracted with ethyl acetate (3×100 ml) and the organic layers combined and dried over anhydrous magnesium sulfate. The organic layers were concentrated under vacuum to give a residue, which was purified by a silica gel column with 2%~5% ethyl acetate in petroleum ether to produce 4-chloro-5-(4-fluoro-2-methylphenoxy)-2-nitroaniline as a yellow solid (1.3 g, 30%). Next, to a solution of 4-chloro-5-(2,4-difluorophenoxy)-2-nitroaniline (1.3 g, 4.32 mmol) in ethanol (20 ml) was added hydrogen chloride (conc. 1 ml) followed by the addition of Zn powder (1.7 g, 25.92 mmol) in portions at room temperature. The resulting solution was stirred for 4 h at 85° C. The resulting mixture was concentrated under vacuum and dissolved in water (150 ml), adjusted pH to 8 with aqueous sodium bicarbonate. The mixture was extracted with ethyl acetate (3×100 ml), dried and concentrated under reduced pressure to give a residue, which was purified by a silica gel column with 10%~20% ethyl acetate in petroleum ether to produce 4-chloro-5-(2,4-difluorophenoxy)benzene-1,2-diamine as a light yellow solid (600 mg, 51%). Finally, a solution of 4-chloro-5-(2,4-difluorophenoxy)benzene-1,2-diamine (100 mg, 0.37 mmol) in hydrogen chloride (conc. 2 ml) and TFA (10 ml) was stirred overnight at 80° C. The solution was quenched with water (100 ml), adjusted pH value of the solution to 7 with aqueous sodium bicarbonate and extracted with ethyl acetate (3×50 ml) and the organic layers combined and dried over anhydrous magnesium sulfate. The solids were filtered out. The resulting mixture was concentrated under vacuum to give a residue, which was purified by a silica gel column with 5%~10% ethyl acetate in petroleum ether to produce 5-chloro-6-(2,4-difluorophenoxy)-2-(trifluoromethyl)-1H-1,3-benzodiazole as a white solid (73.5 mg, 57%).

Compound number 278 was prepared as follows.

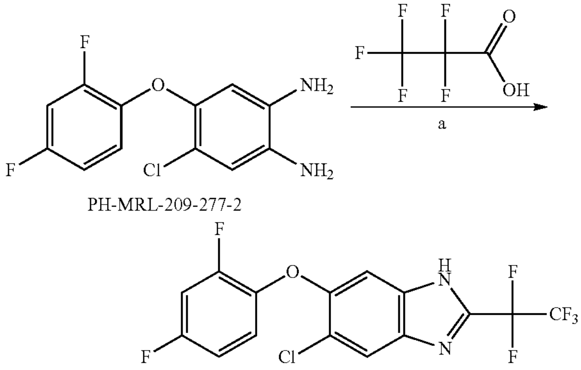

PH-MRL-209-278-0

Reagents and conditions: (a) 80° C., overnight, 16%

A solution of 4-chloro-5-(2,4-difluorophenoxy)benzene-1,2-diamine (100 mg, 0.37 mmol) in pentafluoropropanoic acid (2 ml) was stirred overnight at 80° C. Then the mixture was poured into water (100 ml), adjusted pH to 7 with aqueous sodium bicarbonate and extracted with ethyl acetate (3×50 ml). The combined organic layers were dried over anhydrous sodium sulfate and concentrated under vacuum to give a residue, which was purified by a silica gel column with 5% ethyl acetate in petroleum ether to produce 5-chloro-6-(2,4-difluorophenoxy)-2-(pentafluoroethyl)-1H-1,3-benzodiazole as a white solid (24 mg, 16%).

Compound number 279 was prepared as follows.

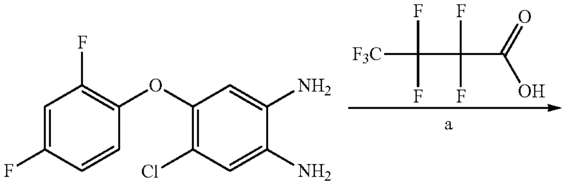

PH-MRL-209-277-2

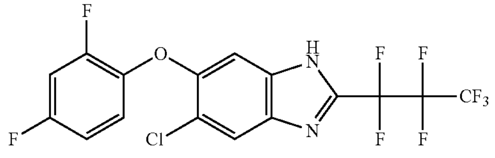

PH-MRL-209-279-0

Reagents and conditions: (a) 90° C., overnight, 21%

A solution of 4-chloro-5-(2,4-difluorophenoxy)benzene-1,2-diamine (100 mg, 0.37 mmol) in heptafluorobutanoic acid (2 ml) was stirred overnight at 90° C. The mixture was poured into water (100 ml), adjusted pH value of the solution to 8 with sodium bicarbonate (solution) and extracted with ethyl acetate (3x50 ml). The combined organic layers were dried over anhydrous sodium sulfate and concentrated under vacuum to give a residue, which was purified by a silica gel column with 10% ethyl acetate in petroleum ether to produce 5-chloro-6-(2,4-difluorophenoxy)-2-(heptafluoropropyl)-1H-1,3-benzodiazole as a pink solid (34.1 mg, 21%).

Compound number 280 was prepared as follows.

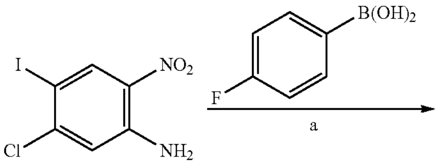

PH-MRL-209-274-1

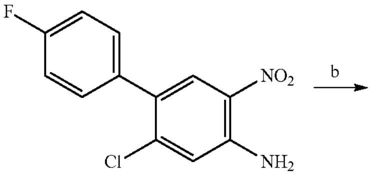

PH-MRL-209-280-1

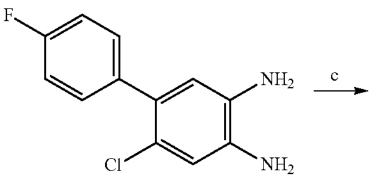

PH-MRL-209-280-2

-continued

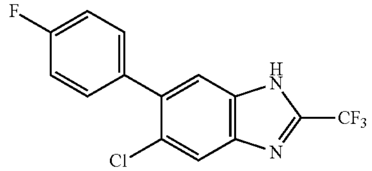

PH-MRL-209-280-0

Reagents and conditions: (a) $K_3PO_4$, $Pd(PPh_3)_4$, $H_2O$, dioxane, 95° C., 8 h, 91%; (b) Zn, HCl (conc), EtOH, reflux, 3 h, 70%; (c) HCl (conc):TFA (16%, v:v), 80° C., overnight, 38%

To a solution of 5-chloro-4-iodo-2-nitroaniline (5 g, 16.75 mmol) in dioxane (200 ml) was added (4-fluorophenyl)boronic acid (4.7 g, 33.59 mmol), water (20 ml), $K_3PO_4$ (7 g, 32.98 mmol), $Pd(PPh_3)_4$ (924 mg, 0.80 mmol) with an inert atmosphere of nitrogen. The resulting solution was stirred for 8 h at 95° C. and then concentrated under reduced pressure to give a residue, which was purified by a silica gel column with 5% to 20% ethyl acetate in petroleum ether to produce 5-chloro-4-(4-fluorophenyl)-2-nitroaniline as a yellow solid (4.1 g, 91%). Next, a solution of 5-chloro-4-(4-fluorophenyl)-2-nitroaniline (4.1 g, 15.38 mmol) in ethanol (100 ml) was added to hydrogen chloride (4 ml, 48 mmol, conc) and Zn (6 g, 460 mmol) at room temperature. The resulting solution was stirred for 3 h at 85° C. The resulting mixture was concentrated under vacuum and dissolved in water (200 ml), adjusted pH to 8 with aqueous sodium bicarbonate and extracted with dichloromethane (3x200 ml). The combined organic layers were dried over anhydrous magnesium sulfate and concentrated under reduced pressure to give a residue, which was purified by a silica gel column with 5% to 10% ethyl acetate in petroleum ether to produce 4-chloro-5-(4-fluorophenyl)benzene-1,2-diamine as a brown oil (2.5 g, 70%). Finally, a solution of 4-chloro-5-(4-fluorophenyl)benzene-1,2-diamine (100 mg, 0.42 mmol) in hydrogen chloride (1 ml) and trifluoroacetic acid (5 ml) was stirred overnight at 80° C. The reaction was quenched by the addition of water (50 ml) and the pH value of the solution adjusted to 7 with aqueous sodium bicarbonate. The resulting solution was extracted with ethyl acetate (3x50 ml) and the organic layers combined and dried over anhydrous magnesium sulfate and concentrated under reduced pressure to give a residue, which was purified by Pre-TLC with 10% ethyl acetate in petroleum ether to produce 5-chloro-6-(4-fluorophenyl)-2-(trifluoromethyl)-1H-1,3-benzodiazole as a white solid (50.7 mg, 38%).

Compound number 281 was prepared as follows.

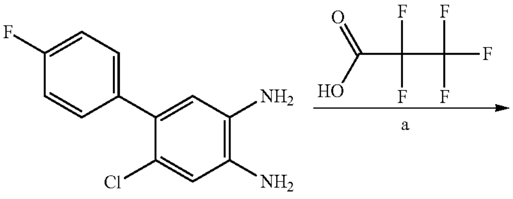

PH-MRL-209-280-2

-continued

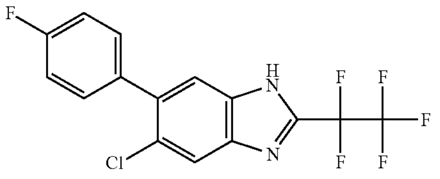

PH-MRL-209-281-0

Reagents and conditions: (a) 80° C., 10 h, 43%

A solution of 4-chloro-5-(4-fluorophenyl)benzene-1,2-diamine (200 mg, 0.85 mmol) in pentafluoropropanoic acid (2 ml) was stirred for 10 h at 80° C. The reaction was then quenched by the addition of water (100 ml), pH adjusted to 7 with saturated aqueous sodium bicarbonate and extracted with ethyl acetate (3×100 ml). The combined organic layers were dried over anhydrous sodium sulfate and concentrated under reduced pressure to give a residue, which was purified by Pre-TLC with 10% ethyl acetate in petroleum ether to produce 5-chloro-6-(4-fluorophenyl)-2-(pentafluoroethyl)-1H-1,3-benzodiazole as a white solid (132.4 mg, 43%).

Compound number 282 was prepared as follows.

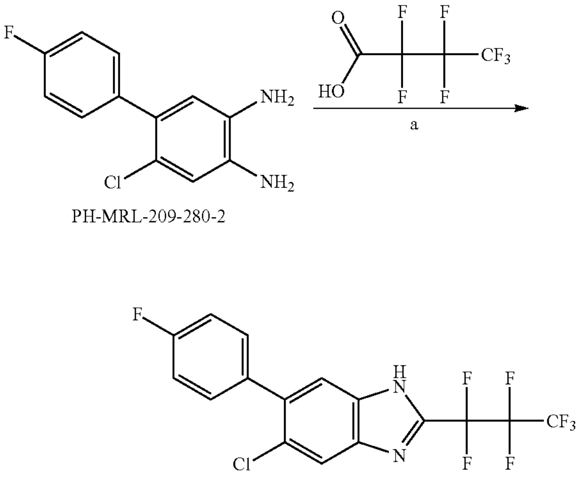

PH-MRL-209-280-2

PH-MRL-209-282-0

Reagents and conditions: (a) 80° C., overnight, 33%

A solution of 4-chloro-5-(4-fluorophenyl)benzene-1,2-diamine (200 mg, 0.85 mmol) in heptafluorobutanoic acid (1.5 ml) was stirred overnight at 80° C. The reaction was then quenched by the addition of water (100 ml), adjusted to pH 7 with saturated aqueous sodium bicarbonate. The resulting solution was extracted with ethyl acetate (3×50 ml) and the organic layers were combined and dried over anhydrous sodium sulfate. The solids were filtered out. The resulting mixture was concentrated under vacuum to give a residue, which was purified by Pre-TLC with 10% ethyl acetate in petroleum ether to produce 5-chloro-6-(4-fluorophenyl)-2-(heptafluoropropyl)-1H-1,3-benzodiazole as a white solid (116.6 mg, 33%).

Compound number 283 was prepared as follows.

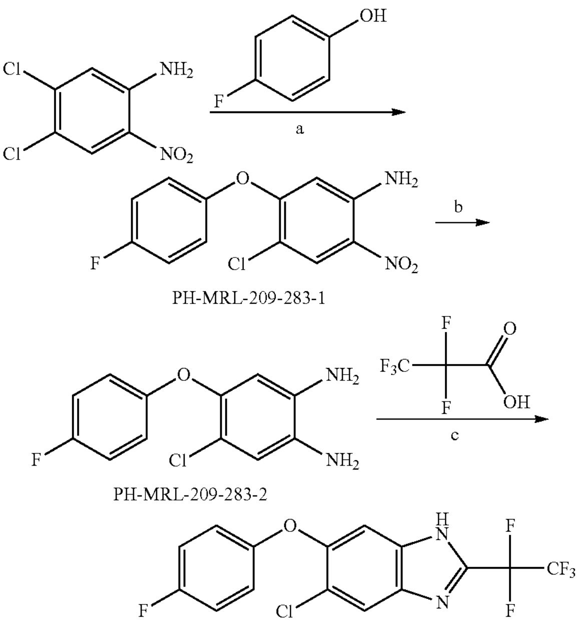

PH-MRL-209-283-1

PH-MRL-209-283-2

PH-MRL-209-283-0

Reagents and conditions: (a) $K_2CO_3$, DMSO, 90° C., overnight, 48%; (b) Zn, HCl (conc), EtOH, rt~reflux, 4 h, 84%; (c) 95° C., overnight, 3%

To a solution of 4-fluorophenol (1.63 g, 14.54 mmol) in DMSO (20 ml) was added 4,5-dichloro-2-nitroaniline (3 g, 14.49 mmol) and potassium carbonate (4 g, 28.94 mmol) with stirring overnight at 90° C. The reaction was then quenched by the addition of water (200 ml), extracted with ethyl acetate (3×100 ml) and dried over anhydrous magnesium sulfate. The solids were filtered out and the filtrate was concentrated under vacuum to give a residue, which was purified by a silica gel column with 2% to 10% ethyl acetate in petroleum ether to produce 4-chloro-5-(4-fluorophenoxy)-2-nitroaniline as a yellow solid (2.0 g, 49%). Next, to a solution of 4-chloro-5-(4-fluorophenoxy)-2-nitroaniline (2 g, 7.08 mmol) and hydrogen chloride (1.8 ml) and ethanol (25 ml) was added Zn powder (2.8 g) in portions at room temperature. The resulting solution was stirred for 4 h at 85° C. and then concentrated under vacuum. The residue was dissolved in water (300 ml), pH adjusted to 8 with aqueous sodium bicarbonate and extracted with ethyl acetate (3×80 ml). The combined organic layers were dried and concentrated under reduced pressure to give a residue, which was purified by a silica gel column with 10% ethyl acetate in petroleum ether to produce 4-chloro-5-(4-fluorophenoxy)benzene-1,2-diamine as red oil (1 g, 83%). Finally, a solution of 4-chloro-5-(4-fluorophenoxy)benzene-1,2-diamine (400 mg, 1.58 mmol) in 2,2-difluoro-3,3-dimethylbutanoic acid (4 ml) was stirred overnight at 95° C. in an oil bath. Then the solution was poured into water (100 ml), adjusted to pH 8 with saturated aqueous sodium bicarbonate and extracted with ethyl acetate (3×50 ml). The combined organic layers were dried over anhydrous sodium sulfate and concentrated under vacuum to give a residue, which was purified by a silica gel column with 10% ethyl acetate in petroleum ether to produce 5-chloro-6-(4-fluorophenoxy)-2-(pentafluoroethyl)-1H-1,3-benzodiazole as a white solid (19.9 mg, 3%).

Compound number 284 was prepared as follows.

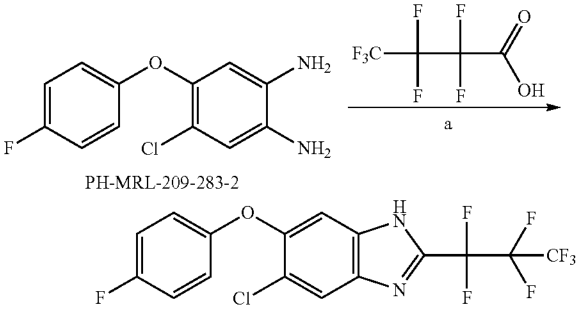

PH-MRL-209-284-0

Reagents and conditions: (a) 110° C., overnight, 2%

A solution of 4-chloro-5-(4-fluorophenoxy)benzene-1,2-diamine (400 mg, 1.58 mmol) in heptafluorobutanoic acid (3 ml) was stirred overnight at 110° C. in an oil bath. The solution was poured into water (150 ml), adjusted pH to 8 with saturated aqueous sodium bicarbonate and extracted with ethyl acetate (3×100 ml). The combined organic layers were concentrated under vacuum to give a residue, which was purified by a silica gel column with 10% ethyl acetate in petroleum ether to produce 5-chloro-6-(4-fluorophenoxy)-2-(heptafluoropropyl)-1H-1,3-benzodiazole as a off-white solid (12.0 mg, 2%).

Compound number 285 was prepared as follows.

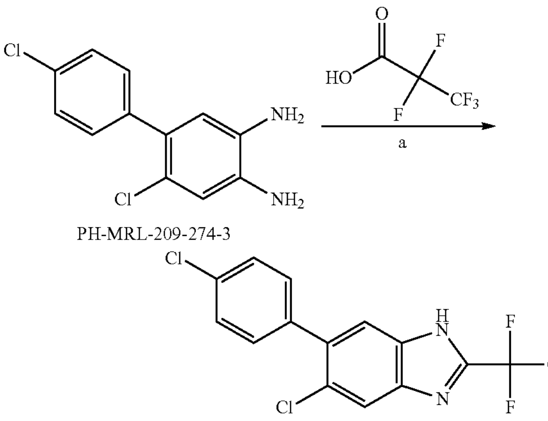

PH-MRL-209-285-0

Reagents and conditions: (a) HCl (conc), 100° C., overnight, 40%

To a solution of 4-chloro-5-(4-chlorophenyl)benzene-1,2-diamine (100 mg, 0.40 mmol) in pentafluoropropanoic acid (5 ml) was added hydrogen chloride (conc) (1 ml). The resulting solution was stirred overnight at 100° C. and then poured into water (50 ml), adjusted pH value of the solution to 8 with sodium bicarbonate (sat). The resulting solution was extracted with ethyl acetate (3×30 ml), combined and dried over anhydrous magnesium sulfate and concentrated under vacuum to give a residue, which was purified by a silica gel column with 8% ethyl acetate in petroleum ether to produce 5-chloro-6-(4-chlorophenyl)-2-(pentafluoroethyl)-1H-1,3-benzodiazole as a white solid (60.8 mg, 40%).

Compound number 286 was prepared as follows.

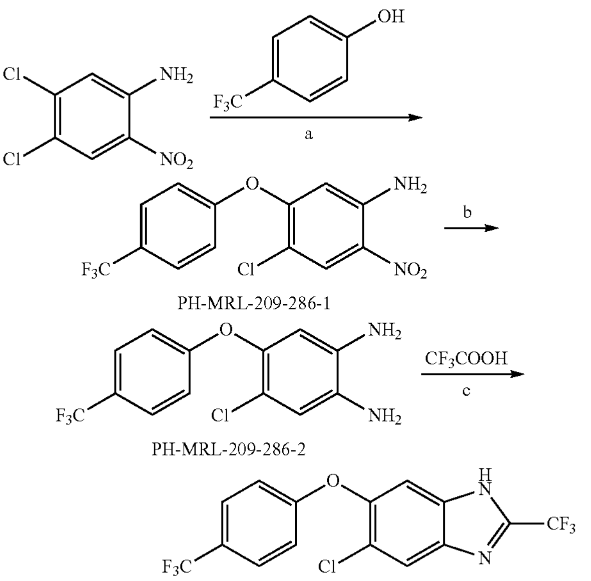

PH-MRL-209-286-0

Reagents and conditions: (a) $K_2CO_3$, DMSO, 90° C., 8 h, 18%; (b) Zn, HCl (conc), EtOH, rt~reflux, 1.5 h, 79%; (c) HCl (conc), 80° C., 4.5 h, 62%

To a solution of 4,5-dichloro-2-nitroaniline (5 g, 24.15 mmol) in DMSO (15 ml) was added potassium carbonate (6.62 g, 47.90 mmol) and 4-(trifluoromethyl)phenol (6.6 g, 40.71 mmol) in several batches. The resulting solution was stirred for 8 h at 90° C. in an oil bath maintained with an inert atmosphere of nitrogen. The reaction mixture was then quenched by the addition of water (200 ml), extracted with ethyl acetate (5×100 ml) and the organic layers combined. The resulting mixture was washed with sodium chloride (3×100 m), dried over anhydrous sodium sulfate and concentrated under vacuum to give a residue, which was purified by a silica gel column with 2% to 10% ethyl acetate in petroleum ether to produce 4-chloro-2-nitro-5-[4-(trifluoromethyl)phenoxy]aniline as a yellow solid (1.43 g, 18%). Next, to a solution of 4-chloro-2-nitro-5-[4-(trifluoromethyl)phenoxy]aniline (499 mg, 1.50 mmol) in ethanol (30 ml) was added hydrogen chloride (conc) (0.4 mL) and Zn powder (586 mg) in several bacthes. The resulting solution was stirred for 1.5 h at 85° C. in an oil bath and then concentrated under vacuum. The residue was dissolved in ethyl acetate (150 ml), washed with saturated aqueous sodium bicarbonate, dried over anhydrous sodium sulfate and concentrated under vacuum. The residue was purified by a silica gel column with 2% to 10% ethyl acetate in petroleum ether to afford 4-chloro-5-[4-(trifluoromethyl)phenoxy]benzene-1,2-diamine as a red solid (359 mg, 79%). Finally, a solution of 4-chloro-5-[4-(trifluoromethyl)phenoxy]benzene-1,2-diamine (100 mg, 0.33 mmol) in trifluoroacetic acid (5 ml) and HCl ((conc), 1 ml) was stirred for 4.5 h at 80° C. in an oil bath. The solution was poured into water (100 ml), adjusted pH value of the solution to 8 with sodium bicarbonate (sat) and extracted with ethyl acetate (3×50 ml). The combined organic layers were dried over anhydrous sodium sulfate and concentrated under vacuum to give a residue, which was purified by Pre-TLC with 11% ethyl acetate in petroleum ether to produce 5-chloro-2-(trifluoromethyl)-6-[4-(trifluoromethyl)phenoxy]-1H-1,3-benzodiazole as a white solid (78.2 mg, 62%).

Compound number 287 was prepared as follows.

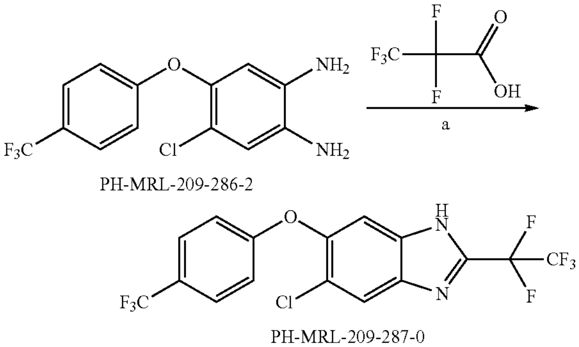

PH-MRL-209-286-2

PH-MRL-209-287-0

Reagents and conditions: (a) 80° C., overnight, 50%

A solution of 4-chloro-5-[4-(trifluoromethyl)phenoxy]benzene-1,2-diamine (200 mg, 0.66 mmol) in pentafluoropropanoic acid (2 ml) was stirred overnight at 80° C. in an oil bath. The solution was poured into water (50 ml), adjusted pH to 8 with sodium bicarbonate (sat) and extracted with ethyl acetate (3×50 ml). The combined organic layers were dried over anhydrous sodium sulfate and concentrated under vacuum to give a residue, which was purified by a silica gel column with 8% ethyl acetate in petroleum ether to produce 5-chloro-2-(pentafluoroethyl)-6-[4-(trifluoromethyl)phenoxy]-1H-1,3-benzodiazole as a white solid (141.7 g, 49.7%).

Compound number 288 was prepared as follows.

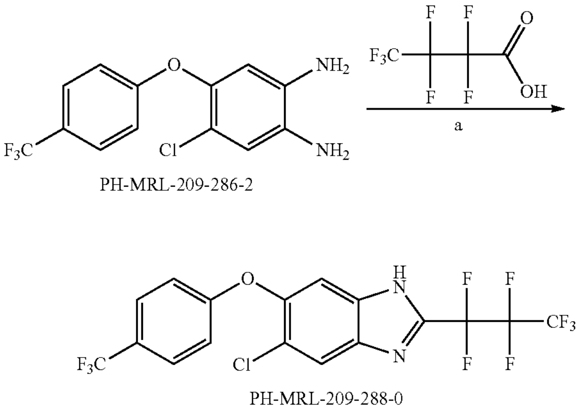

PH-MRL-209-286-2

PH-MRL-209-288-0

Reagents and conditions: (a) 80° C., overnight, 43%

A solution of 4-chloro-5-[4-(trifluoromethyl)phenoxy]benzene-1,2-diamine (200 mg, 0.66 mmol) in heptafluorobutanoic acid (3 ml) was stirred overnight at 80° C. in an oil bath. The solution was diluted with ethyl acetate (100 ml), washed with saturated sodium bicarbonate, dried over anhydrous sodium sulfate and concentrated under vacuum. The residue was purified by Pre-TLC with 10% ethyl acetate in petroleum ether to produce 5-chloro-2-(heptafluoropropyl)-6-[4-(trifluoromethyl)phenoxy]-1H-1,3-benzodiazole as a white solid (135.2 mg, 43%).

Compound number 289 was prepared as follows.

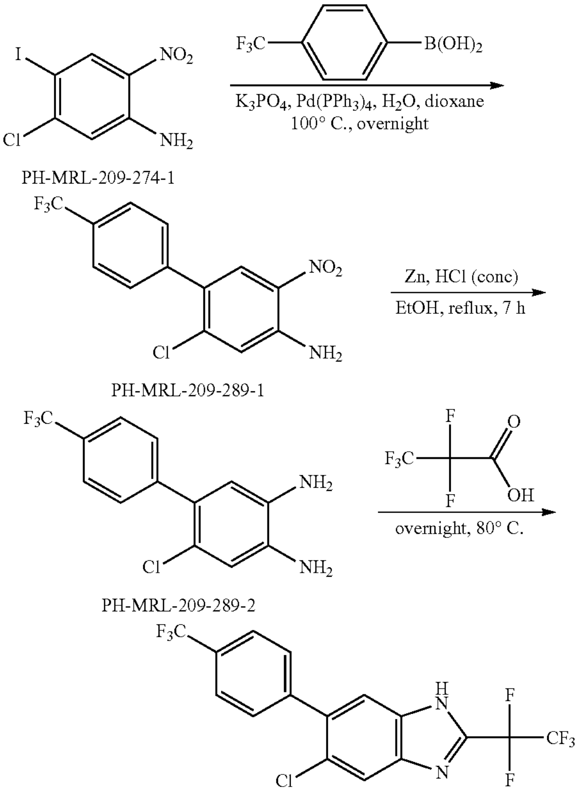

PH-MRL-209-274-1

PH-MRL-209-289-1

PH-MRL-209-289-2

PH-MRL-209-289-0

To a solution of 5-chloro-4-iodo-2-nitroaniline (5.0 g, 16.75 mmol) in dioxane (200 ml) was added water (20 ml), $Pd(PPh_3)_4$ (924 mg, 0.80 mmol), $K_3PO_4$ (7.0 g, 32.98 mmol) and [4-(trifluoromethyl)phenyl]boronic acid (6.3 g, 33.17 mmol) with stirring overnight at 100° C. under nitrogen. The resulting mixture was concentrated under vacuum and dissolved in water (250 ml), extracted with ethyl acetate (3×200 ml) and the organic layers combined, dried over anhydrous sodium sulfate and concentrated under vacuum to give the residue, which was re-crystallized from 50% ether in hexane to afford 5-chloro-2-nitro-4-[4-(trifluoromethyl)phenyl]aniline as a yellow solid (4.2 g, crude). Next, to a solution of 5-chloro-2-nitro-4-[4-(trifluoromethyl)phenyl]aniline (3.7 g, crude) in ethanol (300 ml) and hydrogen chloride (3.0 ml) was added Zn powder (4.55 g, 70.0 mmol) in several bacthes with stirring for 20 min at room temperature. The resulting solution was stirred for 7 h at 85° C. The solids were filtered out and the filtrate was concentrated under vacuum to give a residue, which was dissolved in water (100 ml). The mixture was adjusted to pH 7 with saturated aqueous sodium carbonate, extracted with ethyl acetate (3×300 ml) and the organic layers combined and dried over anhydrous sodium sulfate and concentrated under vacuum to give a residue that was purified by a silica gel column eluted with 10% to 50% ethyl acetate in petroleum ether to produce 4-chloro-5-[4-(trifluoromethyl)phenyl]benzene-1,2-diamine as brown oil (2.9 g,). Finally, the solution of 4-chloro-5-[4-(trifluoromethyl)phenyl]benzene-1,2-diamine (150 mg, 0.52 mmol) in pentafluoropropanoic acid (1 ml) was stirred overnight at 80° C. The result mixture was diluted with water (50 ml) and adjusted to pH 7 with saturated aqueous sodium carbonate. The resulting solution was extracted with ethyl acetate (3×50 ml), combined, dried over anhydrous sodium sulfate and concentrated under vacuum to give a residue, which was purified by a silica gel column eluted with 0.5% to 6.5% ethyl acetate in petroleum ether to produce 5-chloro-2-(pentafluoroethyl)-6-[4-(trifluoromethyl)phenyl]-1H-1,3-benzodiazole as a white solid (112.6 mg, 52%).

Compound number 290 was prepared as follows.

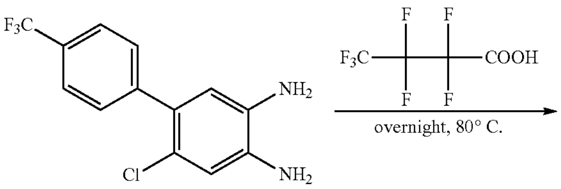

PH-MRL-209-289-2

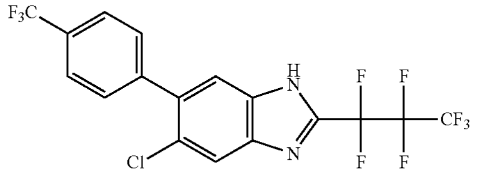

PH-MRL-209-290-0

The solution of 4-chloro-5-[4-(trifluoromethyl)phenyl]benzene-1,2-diamine (250 mg, 0.87 mmol) in heptafluorobutanoic acid (1.5 ml) was stirred overnight at 80° C. The result mixture was diluted with water (50 ml) and adjusted to pH 7 with saturated aqueous sodium carbonate. The resulting solution was extracted with ethyl acetate (3×50 ml), combined and dried over anhydrous magnesium sulfate and concentrated under vacuum to give a residue, which was precipitated from dichloromethane (5 ml) to produce 5-chloro-2-(heptafluoropropyl)-6-[4-(trifluoromethyl)phenyl]-1H-1,3-benzodiazole as a white solid (194.8 mg, 48%).

The compound number 291 was prepared as follows.

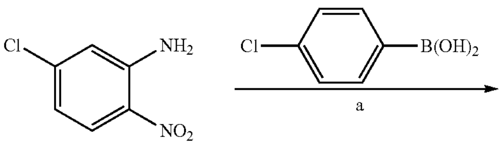

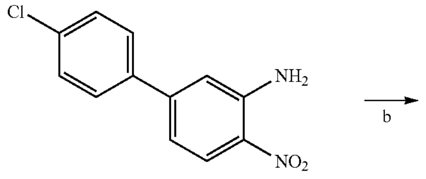

PH-MRL-209-291-1

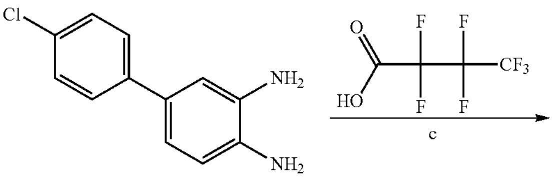

PH-MRL-209-291-2

-continued

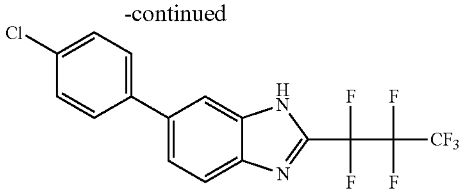

PH-MRL-209-291-0

Reagents and conditions: (a) $K_3PO_4$, $Pd(PPh_3)_4$, $H_2O$, dioxane, 95° C., 4 h, 69%; (b) Zn, HCl (conc), EtOH, reflux, 2 h, 76%; (c) 120° C., 8 h, 18%.

To a solution of 5-chloro-2-nitroaniline (2 g, 11.59 mmol) in dioxane (100 ml) and water (10 ml) was added (4-chlorophenyl)boronic acid (3.6 g, 23.02 mmol), $K_3PO_4$ (5.01 g, 23.18 mmol) and $Pd(PPh_3)_4$ (0.7 g, 0.58 mmol) with stirring for 4 h at 95° C. maintained with an inert atmosphere of nitrogen. Then the resulting mixture was concentrated under vacuum to give a residue, which was purified by a silica gel column with 2% to 5% ethyl acetate in petroleum ether to afford 4-(4-chlorophenyl)-2-nitroaniline as a yellow solid (2.0 g, 69%). Next, to a solution of 5-(4-chlorophenyl)-2-nitroaniline (300 mg, 1.21 mmol) in ethanol (10 ml) was added hydrogen chloride (0.5 ml, 3.63 mmol) and Zn powder (800 mg, 12.3 mmol) in portions at room temperature and stirred for 2 h at 85° C. The resulting mixture was concentrated under vacuum to give a residue and dissolved in water (100 ml), adjusted to pH 8 with aqueous sodium bicarbonate. The mixture was extracted with ethyl acetate (3×100 ml) and dried and concentrated under vacuum to give a residue, which was purified by a silica gel column with 10% to 20% ethyl acetate in petroleum ether to produce 4-(4-chlorophenyl)benzene-1,2-diamine as an off-white solid (200 mg, 76%). Finally, a solution of 4-(4-chlorophenyl)benzene-1,2-diamine (150 mg, 0.69 mmol) in heptafluorobutanoic acid (2 ml) was stirred for 8 h at 120° C. Then the reaction was quenched with water (50 ml), adjusted to pH 7 with sodium bicarbonate and extracted with ethyl acetate(3×100 ml). The combined organic layers were dried over anhydrous magnesium sulfate and concentrated under vacuum to give a residue, which was purified by a silica gel column with 5% to 10% ethyl acetate in petroleum ether to produce 6-(4-chlorophenyl)-2-(heptafluoropropyl)-1H-1,3-benzodiazole as a white solid (49.5 mg, 18%).

Compound number 295 was prepared as follows.

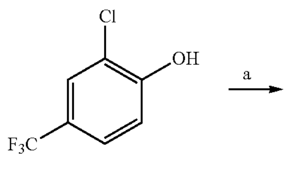

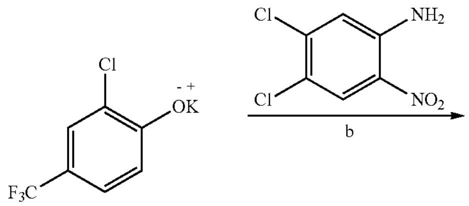

-continued

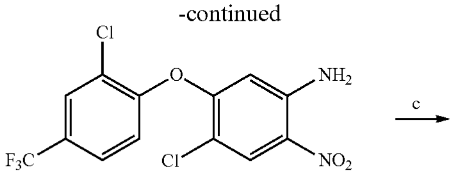

PH-MRL-209-295-1

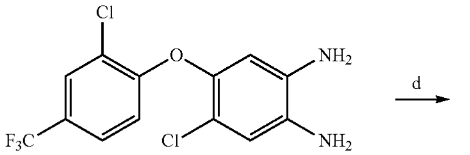

PH-MRL-209-295-2

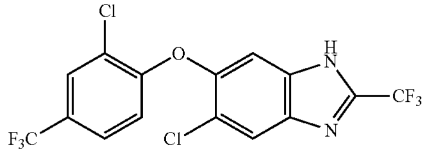

PH-MRL-209-295-0

Reagents and conditions: (a) $K_2CO_3$, DMSO, r.t, overnight; (b) 90° C., overnight; (c) Zn, HCl (conc), EtOH, reflux, 2 h, 61%; (d) TFA, HCl (conc), (v:v = 5:1), reflux, overnight, 59%.

To a solution of 2-chloro-4-(trifluoromethyl)phenol (2 g, 10.18 mmol) in DMSO (250 ml) was added potassium carbonate (4.2 g, 30.17 mmol). The resulting solution was stirred overnight at room temperature, then 4,5-dichloro-2-nitroaniline (2.1 g, 10.14 mmol) was added. The resulting solution was stirred for an additional overnight at 90° C. and then quenched with water (1000 ml) and extracted with ethyl acetate (3×300 ml). The combined organic layers were washed with saturated aqueous brine (3×1000 ml), dried by anhydrous sodium sulfate and concentrated under vacuum to give a residue that was purified by a silica gel column, eluting with 1% to 1.5% ethyl acetate in petroleum ether to produce 4-chloro-5-[2-chloro-4-(trifluoromethyl)phenoxy]-2-nitroaniline as a yellow solid (450 mg, crude). Next, to a solution of 4-chloro-5-[2-chloro-4-(trifluoromethyl)phenoxy]-2-nitroaniline (450 mg, crude) in ethanol (10 ml) was added hydrochloric acid (conc) (0.484 ml) and Zn (478 mg, 7.35 mmol) in several batches at room temperature. The resulting solution was stirred for 10 min at room temperature and 2 h at 80° C. The reaction was concentrated under vacuum and dissolved in water (200 ml), pH adjusted to 8 with potassium carbonate and extracted with ethyl acetate (3×50 ml). The combined organic layers were dried over anhydrous sodium sulfate and concentrated under vacuum to give a residue, which was purified by Prep-HPLC to produce 4-chloro-5-[2-chloro-4-(trifluoromethyl)phenoxy]benzene-1,2-diamine as a off-white solid (150 mg, 61%). Finally, a solution of 4-chloro-5-[2-chloro-4-(trifluoromethyl)phenoxy]benzene-1,2-diamine (50 mg, 0.15 mmol) in trifluoroacetic acid (5 ml) and conc. HCl (1 ml) was refluxed overnight. The reaction was then quenched with water (100 ml), pH value adjusted to 8 with sodium bicarbonate and extracted with ethyl acetate (3×50 ml). The combined organic layers were dried over anhydrous sodium sulfate and concentrated under vacuum to give a residue, which was purified by Prep-TLC with 12.5% ethyl acetate in petroleum ether to produce 5-chloro-6-[2-chloro-4-(trifluoromethyl)phenoxy]-2-(pentafluoroethyl)-1H-1,3-benzodiazole as a white solid (36.4 mg, 53%).

Compound number 296 was prepared as follows.

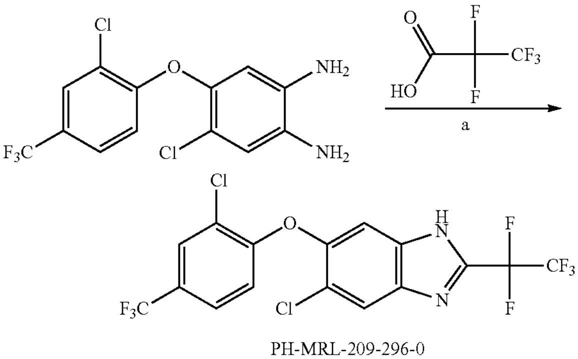

PH-MRL-209-296-0

Reagents and conditions: (a) 80° C., overnight, 55%.

A solution of 4-chloro-5-[2-chloro-4-(trifluoromethyl)phenoxy]benzene-1,2-diamine (50 mg, 0.15 mmol) in pentafluoropropanoic acid (3 ml) was stirred overnight at 80° C. The reaction was then quenched by the addition of water (100 ml), pH value adjusted to 8 with potassium carbonate and extracted with ethyl acetate (3×50 ml). The combined organic layers were dried over anhydrous sodium sulfate and concentrated under vacuum to give a residue, which was purified by Prep-HPLC to produce 5-chloro-6-[2-chloro-4-(trifluoromethyl)phenoxy]-2-(pentafluoroethyl)-1H-1,3-benzodiazole as a pink solid (38 mg, 55%).

Compound number 297 was prepared as follows.

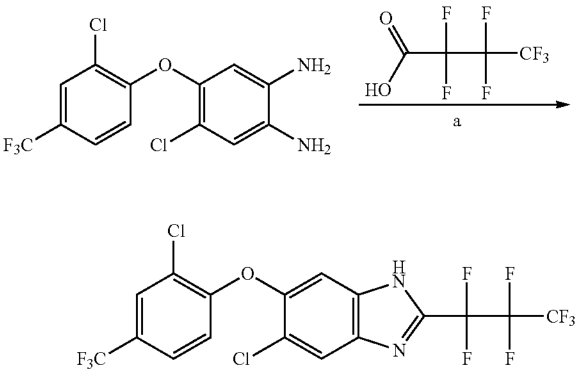

Reagents and conditions: (a) 80° C., overnight, 54%.

To a solution of 4-chloro-5-[2-chloro-4-(trifluoromethyl)phenoxy]benzene-1,2-diamine (50 mg, 0.15 mmol) was added heptafluorobutanoic acid (3 ml). The resulting solution was stirred overnight at 80° C. and quenched with the addition of water (100 ml). The pH value of the solution was adjusted to 8 with potassium carbonate, extracted with ethyl acetate (3×50 ml), organic layers combined, dried over anhydrous sodium sulfate and concentrated under vacuum to give a residue which was purified by Prep-HPLC to produce 5-chloro-6-[2-chloro-4-(trifluoromethyl)phenoxy]-2-(pentafluoroethyl)-1H-1,3-benzodiazole as a light yellow solid (41.2 mg, 54%).

Compound number 301 was prepared as follows.

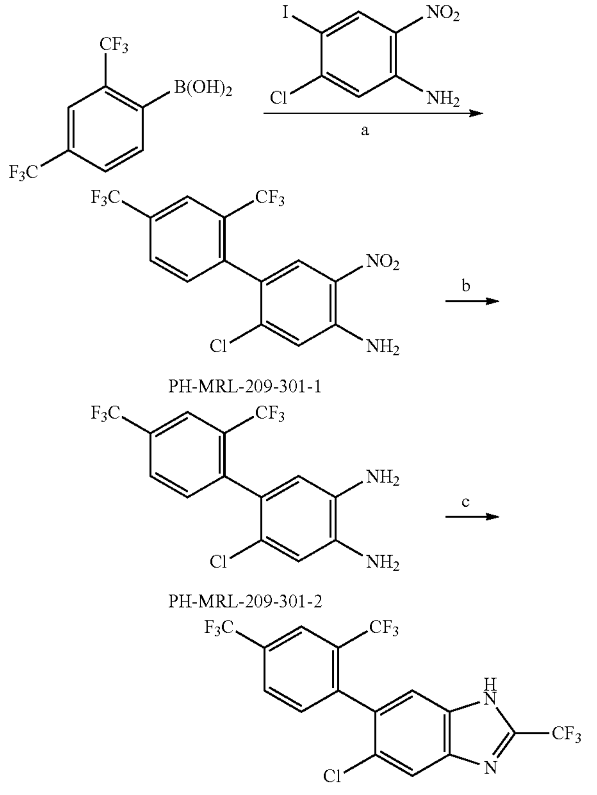

PH-MRL-209-301-0

Reagents and conditions: (a) $K_3PO_4$, $Pd(PPh_3)_4$, $H_2O$, dioxane, 95° C., overnight; (b) Zn, HCl (conc), EtOH, 85° C., 2 h; (c) TFA, HCl (conc), 80° C., overnight, 36%

To a solution of 5-chloro-4-iodo-2-nitroaniline (6 g, 20.1 mmol) in dioxane (100 ml) and water (10 ml) which was purged and maintained with an inert atmosphere of nitrogen was added[2,4-bis(trifluoromethyl)phenyl]boronic acid (10.3 g, 40.01 mmol), $K_3PO_4$ (8.6 g, 40.70 mmol) and $Pd(pph_3)_4$ (2.3 g, 2.04 mmol) at room temperature. The resulting solution was stirred overnight at 95° C. in an oil bath. The resulting mixture was concentrated under vacuum to give a residue, which was purified by a silica gel column, eluting with 2% to 3% ethyl acetate in petroleum ether to produce 4-[2,4-bis(trifluoromethyl)phenyl]-5-chloro-2-nitroaniline as a crude light yellow solid (2.2 g, crude). Next, to a solution of 4-[2,4-bis(trifluoro-methyl)phenyl]-5-chloro-2-nitroaniline (2.2 g, crude) in ethanol (50 ml) was added hydrogen chloride (conc, 1.5 ml) and Zn powder (2.2 g, 33.85 mmol). The resulting solution was stirred for 2 h at 90° C. in an oil bath. The reaction was then quenched by the addition of water (300 ml), adjusted pH to 8 with aqueous sodium carbonate and then extracted with ethyl acetate (3×100 ml). The combined organic layers were washed with brine (200 ml), dried and concentrated under vacuum to produce 4-[2,4-bis (trifluoromethyl) phenyl]-5-chlorobenzene-1,2-diamine as a crude brown solid (1.75 g, crude). Finally, a Solution of 4-[2,4-bis(trifluoromethyl)phenyl]-5-chlorobenzene-1,2-diamine (300 mg, crude) in trifluoroacetic acid (10 ml) and hydrogen chloride (conc, 2 ml) was stirred overnight at 80° C. in an oil bath. The solution was evaporated and dissolved in water (30 ml), adjusted to pH 8 with aqueous sodium carbonate and extracted with ethyl acetate (3×50 ml). The combined organic layers were dried over anhydrous sodium sulfate and concentrated under vacuum to give a residue, which was purified by a silica gel column with 10% ethyl acetate in petroleum ether to produce 6-[2,4-bis(trifluoromethyl)phenyl]-5-chloro-2-(trifluoromethyl)-1H-1,3-benzodiazole as a off-white solid (132.4 mg).

Compound number 302 was prepared as follows.

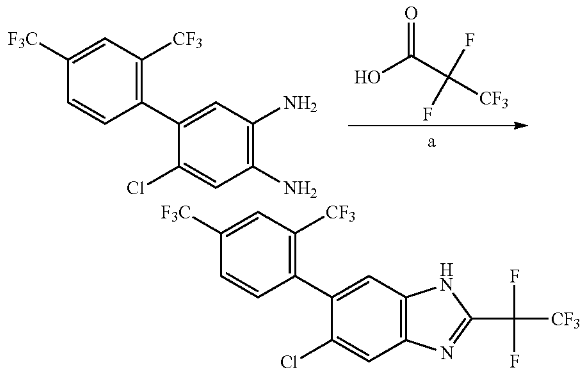

PH-MRL-209-302-0

Reagents and conditions: (a) 80° C., overnight, 19%

A solution of 4-[2,4-bis(trifluoromethyl)phenyl]-5-chlorobenzene-1,2-diamine (300 mg, crude) in pentafluoropropanoic acid (20 ml) was stirred overnight at 80° C. in an oil bath and then quenched with ice-water (50 ml). The pH value of the solution was adjusted to 8 with sodium carbonate and extracted with ethyl acetate (50 ml×3). The combined organic layer was dried over anhydrous sodium sulfate and concentrated under vacuum to give a residue, which was purified by Pre-TLC with 10% ethyl acetate in petroleum ether to produce 6-[2,4-bis(trifluoromethyl)phenyl]-5-chloro-2-(pentafluoroethyl)-1H-1,3-benzodiazole as a off-white solid (76.1 mg).

Compound number 303 was prepared as follows.

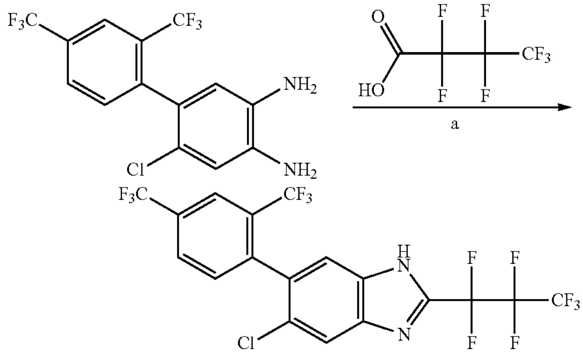

Reagents and conditions: (a) 80° C., overnight, 31%.

A solution of 4-[2,4-bis(trifluoromethyl)phenyl]-5-chlorobenzene-1,2-diamine (300 mg, 0.85 mmol) in heptafluorobutanoic acid (20 ml) was stirred overnight at 80° C. in an oil bath and then quenched with water (100 ml). The pH value of the solution was adjusted to 8 with sodium carbonate and extracted with ethyl acetate (50 ml×3). The combined organic layers were dried over anhydrous sodium sulfate and concentrated under vacuum to give a residue, which was purified by Pre-TLC with 10% ethyl acetate in petroleum ether to produce 6-[2,4-bis(trifluoromethyl)phenyl]-5-chloro-2-(heptafluoropropyl)-1H-1,3-benzodiazole as a pink solid (137.7 mg, 31%).

Compound number 304 was prepared as follows.

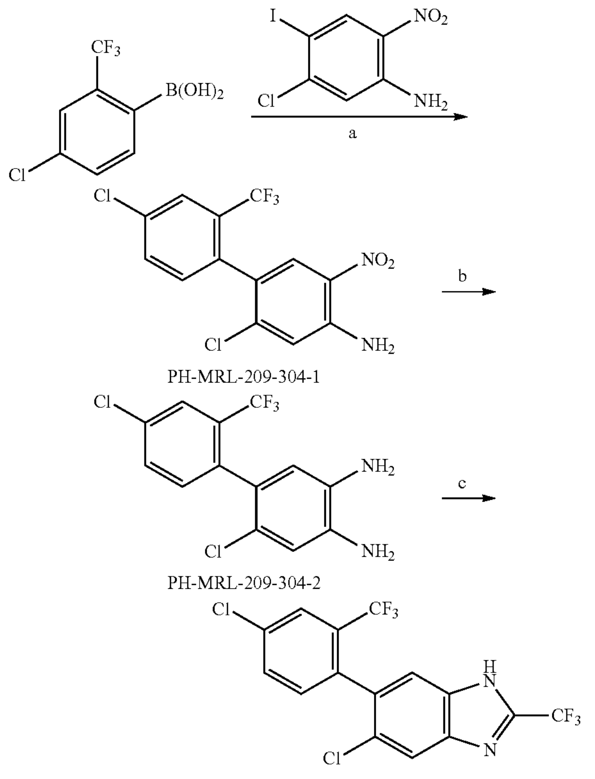

PH-MRL-209-304-1

PH-MRL-209-304-2

PH-MRL-209-304-0

Reagents and conditions: (a) $K_3PO_4$, $Pd(PPh_3)_4$, $H_2O$, dioxane, 95° C., overnight, 50%; (b) Zn, HCl (conc), EtOH, 85° C., 2 h, 26%; (c) TFA, HCl (conc), 85° C., overnight, 82%

To a solution of 5-chloro-4-iodo-2-nitroaniline (2 g, 6.70 mmol) in dioxane (100 ml) and water (10 ml) which maintained with an inert atmosphere of nitrogen was added [4-chloro-2-(trifluoromethyl)phenyl]boronic acid (1.8 g, 8.02 mmol), $K_3PO_4$ (2.6 g, 12.24 mmol), $Pd(PPH_3)_4$ (0.78 g, 335.77 mmol) with stirring overnight at 95° C. in an oil bath. The resulting mixture was concentrated under vacuum to give a residue which was purified by a silica gel column, eluting with 2% to 3% acetate in petroleum ether to produce 5-chloro-4-[4-chloro-2-(trifluoromethyl)phenyl]-2-nitroaniline as a yellow solid (800 mg, 34%). Next, to a solution of 5-chloro-4-[4-chloro-2-(trifluoromethyl)phenyl]-2-nitroaniline (1.6 g, 4.56 mmol) in ethanol (50 ml) was added Zn powder (1.8 g, 27.69 mmol), hydrogen chloride (2 ml) with stirring for 2 h at 85° C. in an oil bath. The solution was poured into water (300 ml), adjusted to pH 8 with saturated aqueous sodium carbonate and extracted with ethyl acetate (3×100 ml). The combined organic layers were washed with brine (100 ml), dried over anhydrous sodium sulfate and concentrated under vacuum to give a residue, which was purified by a silica gel column, eluting with 5% to 20% ethyl acetate in petroleum to produce 4-chloro-5-[4-chloro-2-(trifluoromethyl)phenyl]benzene-1,2-diamine as a crude red solid (560 mg, 76%). Finally, the solution of 4-chloro-5-[4-chloro-2-(trifluoromethyl)phenyl]benzene-1,2-diamine (100 mg, 0.31 mmol) in trifluoroacetic acid (5 m 1) and hydrogen chloride (1 ml) was stirred overnight at 80° C. in an oil bath. The mixture was quenched with water (100 ml), adjusted to pH 8 with saturated aqueous sodium carbonate solution and extracted with ethyl acetate (50 ml×3). The organic layers were dried over anhydrous sodium sulfate and concentrated under vacuum to give a residue, which was purified by a silica gel column with 10% ethyl acetate in petroleum ether to afford 5-chloro-6-[4-chloro-2-(trifluoromethyl)phenyl]-2-(trifluoro methyl)-1H-1,3-benzodiazole as a white solid (101.7 mg, 82%).

Compound number 305 was prepared as follows.

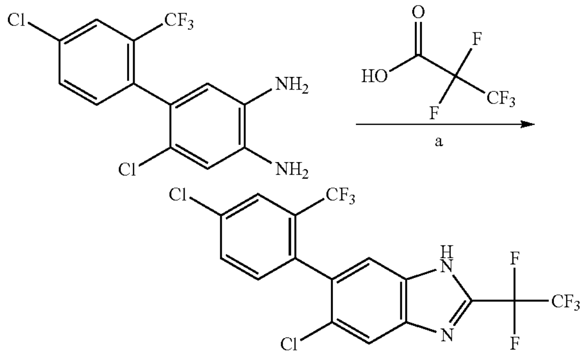

PH-MRL-209-305-0

Reagents and conditions: (a) 80° C., overnight, 77%

A solution of 4-chloro-5-[4-chloro-2-(trifluoromethyl)phenyl]benzene-1,2-diamine (100 mg, 0.31 mmol) in pentafluoropropanoic acid (5 ml) was stirred overnight at 80° C. in an oil bath and then quenched with ice-water (50 ml). The pH value of the solution was adjusted to 8 with saturated aqueous sodium carbonate and extracted with ethyl acetate ((50 ml×3). The combined organic layers were dried over anhydrous sodium sulfate and concentrated under vacuum to give a residue, which was purified by a silica gel column with 10% ethyl acetate in petroleum ether to produce 5-chloro-6-[4-chloro-2-(trifluoromethyl)phenyl]-2-(pentafluoroethyl)-1H-1,3-benzodiazole as a off-white solid (129.8 mg, 77%).

Compound number 306 was prepared as follows.

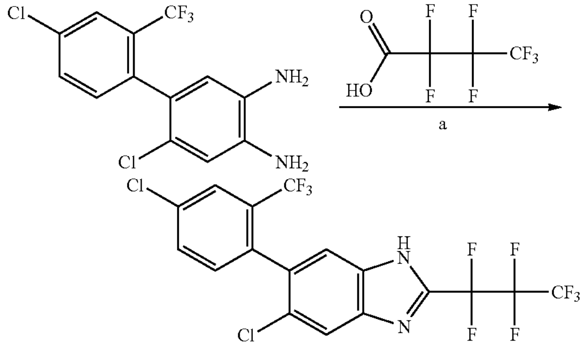

Reagents and conditions: (a) 80° C., overnight, 68%

A solution of 4-chloro-5-[4-chloro-2-(trifluoromethyl)phenyl]benzene-1,2-diamine (100 mg, 0.31 mmol, 1.00 equiv) in heptafluorobutanoic acid (5 ml) was stirred overnight at 80° C. in an oil bath and then quenched with ice-water (30 ml). The pH value of the solution was adjusted to 8 with saturated aqueous sodium carbonate and extracted with ethyl acetate (50 ml×3). The combined organic layers were dried over anhydrous sodium sulfate and concentrated under vacuum to give a residue, which was purified by Pre-TLC with 10% ethyl acetate in petroleum ether to produce 5-chloro-6-[4-chloro-2-(trifluoromethyl)phenyl]-2-(heptafluoropropyl)-1H-1,3-benzodiazole as a off-white solid (105.8 mg, 68%).

Compound number 307 was prepared as follows.

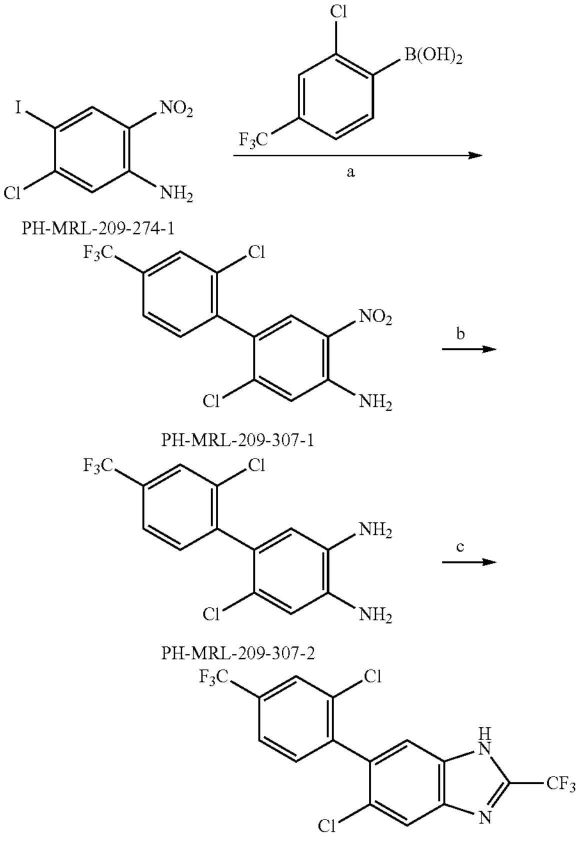

PH-MRL-209-274-1

PH-MRL-209-307-1

PH-MRL-209-307-2

PH-MRL-209-307-0

Reagents and conditions: (a) $K_3PO_4$, $Pd(PPh_3)_4$, $H_2O$, dioxane, overnight, 95° C., 32%; (b) Zn, HCl (conc), EtOH, reflux 2 h, 36%; (c) TFA, HCl (conc, v:v = 5:1), 80° C., overnight, 87%.

To a solution of [2-chloro-4-(trifluoromethyl)phenyl]boronic acid (4.5 g, 20.06 mmol) in water (30 mL) and dioxane (200 mL) was added $K_3PO_4$ (5.7 g, 26.85 mmol), 5-chloro-4-iodo-2-nitroaniline (4 g, 13.40 mmol) and $Pd(PPh_3)_4$ (800 mg, 0.69 mmol) maintained with an inert atmosphere of nitrogen and stirred overnight at 95° C. The resulting mixture was concentrated under vacuum to give a residue, which was purified by a silica gel column with 10% ethyl acetate in petroleum ether to produce 5-chloro-4-[2-chloro-4-(trifluoromethyl)phenyl]-2-nitroaniline as a yellow solid (3 g, 32%). Next, to a solution of 5-chloro-4-[2-chloro-4-(trifluoromethyl)phenyl]-2-nitroaniline (3 g, 8.54 mmol) in ethanol (80 mL) was added hydrochloric acid (2 mL) and Zn powder (3.4 g, 52.3 mmol) in portions. The resulting solution was stirred for 2 h at reflux. The resulting mixture was concentrated under vacuum and dissolved in water (100 ml) adjusted to pH 8 with sodium carbonate and extracted with ethyl acetate (3×100 mL). The combined organic layers were dried over anhydrous sodium sulfate and concentrated under vacuum to give the residue, which was purified by a silica gel column with 20% ethyl acetate in petroleum ether to produce 4-chloro-5-[2-chloro-4-(trifluoromethyl)phenyl]benzene-1,2-diamine as brown oil (1 g, 36%). Finally, the solution of 4-chloro-5-[2-chloro-4-(trifluoromethyl)phenyl]benzene-1,2-diamine (100 mg, 0.31 mmol) in TFA (5 mL) and hydrochloric acid (conc, 1 mL) was stirred overnight at 80° C. and quenched with water (100 ml), adjusted pH to 8 with saturated aqueous sodium carbonate and extracted with ethyl acetate (3×50 mL). The combined organic layers were dried over anhydrous sodium sulfate and concentrated under vacuum to give a residue, which was purified by a silica gel column with 10% ethyl acetate in petroleum ether to produce 5-chloro-6-[2-chloro-4-(trifluoromethyl)phenyl]-2-(trifluoromethyl)-1H-1,3-benzodiazole as a white solid (107.8 mg, 87%).

Compound number 308 was prepared as follows.

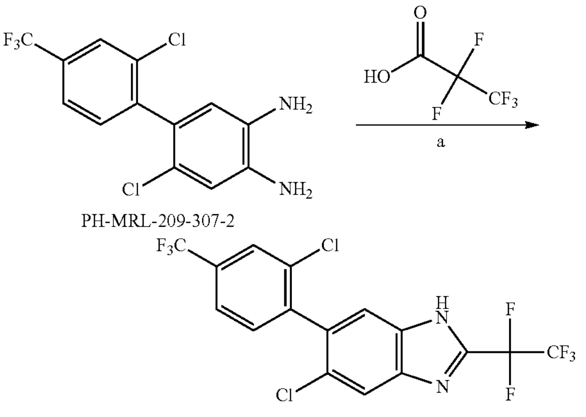

PH-MRL-209-307-2

PH-MRL-209-308-0

Reagents and conditions: (a) 80° C., overnight, 74%

A solution of 4-chloro-5-[2-chloro-4-(trifluoromethyl)phenyl]benzene-1,2-diamine (120 mg, 0.37 mmol), pentafluoropropanoic acid (5 ml) was stirred overnight at 80° C. in an oil bath. Then the mixture was quenched with water (100 ml), pH adjusted to 7 with saturated aqueous sodium carbonate and extracted with ethyl acetate (3×50 ml). The combined organic layers were dried over anhydrous sodium sulfate and concentrated under vacuum to give a residue that was purified by a silica gel column with 10% ethyl acetate in petroleum ether to produce 5-chloro-6-[2-chloro-4-(trifluoromethyl)phenyl]-2-(pentafluoroethyl)-1H-1,3-benzodiazole as a white solid (124.4 mg, 74%).

Compound number 309 was prepared as follows.

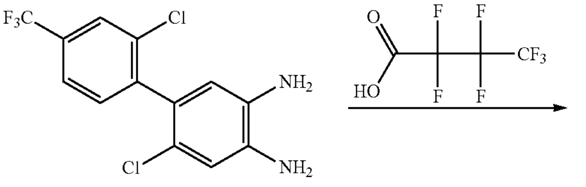

PH-MRL-209-307-2

-continued

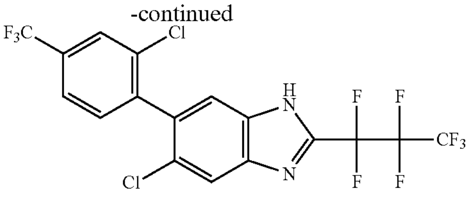

PH-MRL-209-309-0

Reagents and conditions: 80° C., overnight, 54%

A solution of 4-chloro-5-[2-chloro-4-(trifluoromethyl)phenyl]benzene-1,2-diamine (120 mg, 0.37 mmol), heptafluorobutanoic acid (5 ml) was stirred overnight at 80° C. in an oil bath. The solution was diluted with water (100 ml), adjusted to pH 7 with saturated aqueous sodium carbonate and extracted with ethyl acetate (3×50 ml). The combined organic layers were dried over anhydrous sodium sulfate and concentrated under vacuum. The residue was purified by a silica gel column with 10% ethyl acetate in petroleum ether to produce 5-chloro-6-[2-chloro-4-(trifluoromethyl)phenyl]-2-(heptafluoropropyl)-1H-1,3-benzodiazole as a white solid (100.3 mg, 54%).

The invention is further described by the following numbered paragraphs:

1. A compound of the formula:

(I)

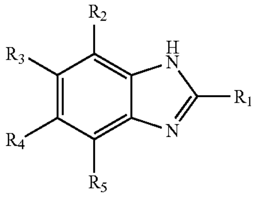

wherein:

$R_1$ is $(C_1-C_6)$-alkyl, $(C_2-C_5)$-alkenyl, or $(C_2-C_5)$-alkynyl, each independently unsubstituted or substituted with two or more halogens;

$R_2$ is H or halogen;

$R_3$ is halogen, $(C_1-C_6)$-alkyl, $(C_2-C_5)$-alkenyl, or $(C_2-C_5)$-alkynyl, $(C_1-C_6)$-alkoxy, thienyl, furanyl, biphenyl, naphthyl, aryl, aryl ether, sulfonylaryl, sulfoxyaryl, thioaryl, $(C_3-C_6)$-cycloalkyl, or tetralin ether;

wherein the last seven substituents may be unsubstituted or substituted with one or more of halogen, $(C_1-C_3)$-haloalkyl, $(C_1-C_3)$-haloalkoxy or carboxyl;

$R_4$ is H or halogen;

$R_5$ is H or halogen.

2. A compound according to claim 1 wherein $R_1$ is $(C_1-C_4)$-alkyl substituted with fluorine.
3. A compound according to claim 1 wherein $R_2$ is Cl.
4. A compound according to claim 1 wherein $R_3$ is a mono- or bi-halogen substituted phenyl ether.
5. A compound according to claim 1 wherein $R_3$ is a bi- or tri-halogen substituted phenyl.
6. A compound according to claim 4 or 5 wherein the halogen is chlorine, bromine or fluorine.
7. A compound according to claim 1 wherein $R_4$ is chlorine.
8. A compound according to claim 1 wherein $R_5$ is hydrogen.
9. A compound according to claim 1 that is 6-chloro-5-(4-chlorophenyl)-2-trifluoromethylbenzimidazole. (#130)
10. A compound according to claim 1 that is 6-chloro-5-(2,3-dichlorophenoxy)-2-heptafluoropropylbenzimidazole. (#140)
11. A compound according to claim 1 that is 6-chloro-5-(3,5-dichlorophenyl)-2-trifluoromethylbenzimidazole. (#247)
12. A compound according to claim 1 that is 6-chloro-5-(3,4-dichlorophenyl)-2-trifluoromethylbenzimidazole. (#258)
13. A compound according to claim 1 that is 6-chloro-5-(2,4-dichlorophenyl)-2-trifluoromethylbenzimidazole. (#260)
14. A compound according to claim 1 that is 6-chloro-5-(2,3,5-trichlorophenyl)-2-trifluoromethylbenzimidazole. (#261)
15. A compound according to claim 1 that is 5-chloro-6-(2,4-dichlorophenoxy)-2-(heptafluoropropyl)-1H-1,3-benzodiazole. (#273)
16. A composition for treating helminth infestation comprising an anthelmintically effective amount of the compound of claim 1, 9, 10, 11, 12, 13, 14 or 15 and a pharmaceutically acceptable carrier.
17. A composition for treating helminth infestation according to claim 16 wherein the composition of formula (I) is combined with an additional active agent.
18. A composition for treating helminth infestation according to claim 17 wherein the active agent is a macrocyclic lactone.
19. A composition for treating helminth infestation according to claim 18 wherein the macrocyclic lactone is selected from the group consisting of abamectin, dimadectin, doramectin, emamectin, eprinomectin, ivermectin, latidectin, lepimectin, selamectin or ML-1,694,554.
20. A composition for treating helminth infestation according to claim 17 wherein the composition of formula (I) is combined with verapamil.
21. A method for treating helminth infestation comprising administration of an anthelmintically effective amount of the compound of claim 1, 9, 10, 11, 12, 13, 14 or 15 to an animal in need thereof.
22. A method according to claim 21 in which the helminths are trematodes.
23. A method according to claim 22 in which the helminths are *Fasciola hepatica.*
24. A compound of the formula:

(II)

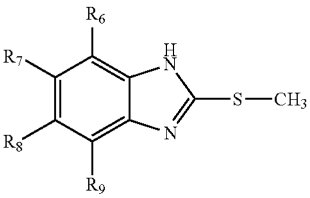

wherein:

$R_6$ is H;

$R_7$ is $(C_1-C_6)$-alkyl, $(C_2-C_5)$-alkenyl, or $(C_2-C_5)$-alkynyl, $(C_1-C_6)$-alkoxy, tetralin ether, bromophenoxy, phenoxy, sulfonylaryl, sulfoxyaryl, thioaryl, or $(C_3-C_6)$-cycloalkyl;

wherein the last four substituents may be unsubstituted or substituted with one or more of halogen or $(C_1-C_3)$-alkyl; and wherein phenoxy is substituted with one or more of $(C_1-C_3)$-alkyl or trifluoromethoxy;

$R_8$ is H or halogen;

$R_9$ is H.

25. A compound according to claim 24 wherein $R_7$ is phenoxy substituted with one or more methyl groups.

26. A compound according to claim 24 wherein $R_7$ is 2-bromophenoxy.

27. A compound according to claim 24 wherein $R_8$ is chlorine or fluorine.

28. A compound according to claim 24 that is 6-chloro-5-(2, 3-dimethylphenoxy)-2-methylthiobenzimidazole. (#19)

29. A compound according to claim 24 that is 6-chloro-5-(2-bromophenoxy)-2-methylthiobenzimidazole. (#14)

30. A compound according to claim 24 that is 6-chloro-5-hexyl-2-methylthiobenzimidazole. (#24)

31. A composition for treating helminth infestation comprising an anthelmintically effective amount of the compound of claim 24, 28, 29 or 30 and a pharmaceutically acceptable carrier.

32. A composition for treating helminth infestation according to claim 31 wherein the composition of formula (I) is combined with an additional active agent.

33. A composition for treating helminth infestation according to claim 32 wherein the active agent is a macrocyclic lactone.

34. A composition for treating helminth infestation according to claim 33 wherein the macrocyclic lactone is selected from the group consisting of abamectin, dimadectin, doramectin, emamectin, eprinomectin, ivermectin, latidectin, lepimectin, selamectin or ML-1,694,554.

35. A composition for treating helminth infestation according to claim 32 wherein the composition of formula (I) is combined with verapamil.

36. A method for treating helminth infestation comprising administration of an anthelmintically effective amount of the compound of claim 24, 28, 29 or 30 to an animal in need thereof.

37. A method according to claim 36 in which the helminths are trematodes.

38. A method according to claim 37 in which the helminths are *Fasciola hepatica.*

39. A compound of the formula:

(III)

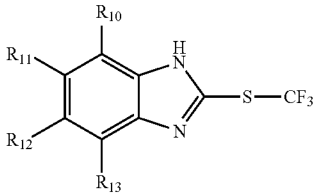

wherein:

$R_{10}$ is H;

$R_{11}$ is ($C_1$-$C_6$)-alkyl, ($C_2$-$C_5$)-alkenyl, or ($C_2$-$C_5$)-alkynyl, ($C_1$-$C_6$)-alkoxy, tetralin ether, aryl, aryl ether, sulfonylaryl, sulfoxyaryl, thioaryl, ($C_3$-$C_6$)-cycloalkyl, or;

wherein the last six substituents may be unsubstituted or substituted with one or more of ($C_1$-$C_6$)-alkyl, halogen, ($C_1$-$C_3$)-haloalkyl, or ($C_1$-$C_3$)-haloalkoxy;

$R_{12}$ is H or halogen;

$R_{13}$ is H.

40. A compound according to claim 39 wherein aryl is naphthyl, biphenyl or phenyl.

41. A compound according to claim 39 wherein $R_{11}$ is phenoxy substituted with one or more halogens.

42. A compound according to claim 39 that is 6-chloro-5-(2, 3-dichlorophenoxy)-2-trifluoromethylthiobenzimidazole. (#49)

43. A compound according to claim 39 that is 6-chloro-5-(4-chlorophenyl)-2-trifluoromethylthiobenzimidazole. (#102)

44. A compound according to claim 39 that is 6-chloro-5-(3-chlorophenyl)-2-trifluoromethylthiobenzimidazole. (#103)

45. A compound according to claim 39 that is 6-chloro-5-(2-butyl)-cyclopropyl-2-trifluoromethylthiobenzimidazole. (#108)

46. A composition for treating helminth infestation comprising an anthelmintically effective amount of the compound of claim 39, 42, 43, 44 or 45 and a pharmaceutically acceptable carrier.

47. A composition for treating helminth infestation according to claim 46 wherein the composition of formula (I) is combined with an additional active agent.

48. A composition for treating helminth infestation according to claim 47 wherein the active agent is a macrocyclic lactone.

49. A composition for treating helminth infestation according to claim 48 wherein the macrocyclic lactone is selected from the group consisting of abamectin, dimadectin, doramectin, emamectin, eprinomectin, ivermectin, latidectin, lepimectin, selamectin or ML-1,694,554.

50. A composition for treating helminth infestation according to claim 47 wherein the composition of formula (I) is combined with verapamil.

51. A method for treating helminth infestation comprising administration of an anthelmintically effective amount of the compound of claim 38, 42, 43, 44 or 45 to an animal in need thereof.

52. A method according to claim 51 in which the helminths are trematodes.

53. A method according to claim 52 in which the helminths are *Fasciola hepatica.*

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound of the formula:

(I)

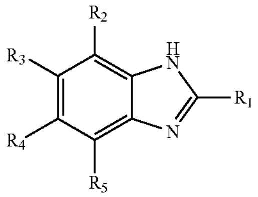

wherein:

$R_1$ is ($C_1$-$C_6$)-alkyl, substituted with two or more halogens;

$R_2$ is H or halogen;

$R_3$ is a bi- or tri-halogen substituted phenyl;

$R_4$ is H or halogen; and $R_5$ is H or halogen.

2. A compound that is 6-chloro-5-(4-chlorophenyl)-2-trifluoromethylbenzimidazole.

3. A compound that is 6-chloro-5-(2,3-dichlorophenoxy)-2-heptafluoropropylbenzimidazole.

4. A compound according to claim 1 that is 6-chloro-5-(3,5-dichlorophenyl)-2-trifluoromethylbenzimidazole.

5. A compound according to claim 1 that is 6-chloro-5-(3,4-dichlorophenyl)-2-trifluoromethylbenzimidazole.

6. A compound according to claim 1 that is 6-chloro-5-(2,4-dichlorophenyl)-2-trifluoromethylbenzimidazole.

7. A compound according to claim 1 that is 6-chloro-5-(2,3,5-trichlorophenyl)-2-trifluoromethylbenzimidazole.

8. A compound that is 5-chloro-6-(2,4-dichlorophenoxy)-2-(heptafluoropropyl)-1H-1,3-benzodiazole.

9. A composition for treating helminth infestation comprising an anthelmintically effective amount of the compound of claim 1 and a pharmaceutically acceptable carrier.

10. A composition for treating helminth infestation according to claim 9 wherein the composition of formula (I) is combined with an additional active agent.

11. A composition for treating helminth infestation according to claim 10 wherein the active agent is a macrocyclic lactone.

12. A composition for treating helminth infestation according to claim 11 wherein the macrocyclic lactone is selected from the group consisting of abamectin, dimadectin, doramectin, emamectin, eprinomectin, ivermectin, latidectin, lepimectin, selamectin and ML-1,694,554.

13. A composition for treating helminth infestation according to claim 10 wherein the composition of formula (I) is combined with verapamil.

14. A method for treating helminth infestation comprising the step of administering an anthelmintically effective amount of the compound of claim 1 to an animal in need thereof.

15. A method according to claim 14 in which the step of administering an anthelmintically effective amount of the compound to an animal in need thereof comprises an animal in which the helminths are trematodes.

16. A method according to claim 15 in which the step of administering an anthelmintically effective amount of the compound to an animal in need thereof comprises an animal in which the helminths are *Fasciola hepatica*.

17. A method for treating helminth infestation comprising the step of administering an anthelmintically effective amount of the compound of claim 3 to an animal in need thereof 18. A method according to claim 17 in which the step of administering an anthelmintically effective amount of the compound to an animal in need thereof comprises an animal in which the helminths are trematodes.

19. A method according to claim 18 in which the step of administering an anthelmintically effective amount of the compound to an animal in need thereof comprises an animal in which the helminths are *Fasciola hepatica*.

20. A composition for treating helminth infestation comprising an anthelmintically effective amount of the compound of claim 2 and a pharmaceutically acceptable carrier.

21. A composition for treating helminth infestation according to claim 20 wherein the composition of formula (I) is combined with an additional active agent.

22. A composition for treating helminth infestation according to claim 21 wherein the active agent is a macrocyclic lactone.

23. A composition for treating helminth infestation according to claim 22 wherein the macrocyclic lactone is selected from the group consisting of abamectin, dimadectin, doramectin, emamectin, eprinomectin, ivermectin, latidectin, lepimectin, selamectin and ML-1,694,554.

24. A composition for treating helminth infestation according to claim 21 wherein the additional active agent is verapamil.

25. A composition for treating helminth infestation comprising an anthelmintically effective amount of the compound of claim 3 and a pharmaceutically acceptable carrier.

26. A composition for treating helminth infestation according to claim 25 wherein the composition of formula (I) is combined with an additional active agent.

27. A composition for treating helminth infestation according to claim 26 wherein the active agent is a macrocyclic lactone.

28. A composition for treating helminth infestation according to claim 27 wherein the macrocyclic lactone is selected from the group consisting of abamectin, dimadectin, doramectin, emamectin, eprinomectin, ivermectin, latidectin, lepimectin, selamectin and ML-1,694,554.

29. A composition for treating helminth infestation according to claim 26 wherein the additional active agent is verapamil.

30. A method for treating helminth infestation comprising the step of administering an anthelmintically effective amount of the compound of claim 2 to an animal in need thereof.

31. A method according to claim 30 in which the step of administering an anthelmintically effective amount of the compound to an animal in need thereof comprises an animal in which the helminths are trematodes.

32. A method according to claim 31 in which the step of administering an anthelmintically effective amount of the compound to an animal in need thereof comprises an animal in which the helminths are *Fasciola hepatica*.

* * * * *